United States Patent
Abdou

(10) Patent No.: US 9,198,767 B2
(45) Date of Patent: Dec. 1, 2015

(54) DEVICES AND METHODS FOR SPINAL STABILIZATION AND INSTRUMENTATION

(71) Applicant: Samy Abdou, San Diego, CA (US)

(72) Inventor: Samy Abdou, San Diego, CA (US)

( * ) Notice: Subject to any disclaimer, the term of this patent is extended or adjusted under 35 U.S.C. 154(b) by 45 days.

(21) Appl. No.: 13/841,373

(22) Filed: Mar. 15, 2013

(65) Prior Publication Data

US 2014/0107783 A1 Apr. 17, 2014

Related U.S. Application Data

(60) Provisional application No. 61/743,162, filed on Aug. 28, 2012, provisional application No. 61/797,177, filed on Dec. 1, 2012.

(51) Int. Cl.
*A61F 2/44* (2006.01)
*A61B 17/70* (2006.01)
*A61B 17/02* (2006.01)

(52) U.S. Cl.
CPC ........... *A61F 2/4405* (2013.01); *A61B 17/7064* (2013.01); *A61B 2017/0256* (2013.01)

(58) Field of Classification Search
CPC ....... A61F 2/44; A61F 2/4405; A61F 2/4611; A61B 17/7064; A61B 17/70; A61B 17/7067; A61B 17/7049; A61B 17/7068; A61B 17/7071; A61B 17/7073
USPC .............................. 623/17.11, 17.16; 606/247
See application file for complete search history.

(56) References Cited

U.S. PATENT DOCUMENTS

| | | | |
|---|---|---|---|
| 8,795,335 B1* | 8/2014 | Abdou et al. | 606/247 |
| 2004/0006391 A1* | 1/2004 | Reiley | 623/17.11 |
| 2004/0254575 A1* | 12/2004 | Obenchain et al. | 606/61 |
| 2008/0132951 A1* | 6/2008 | Reiley et al. | 606/247 |
| 2008/0234735 A1* | 9/2008 | Joshi | 606/247 |
| 2009/0012566 A1* | 1/2009 | Fauth | 606/247 |
| 2012/0010658 A1* | 1/2012 | Kirschman | 606/246 |
| 2014/0188223 A1* | 7/2014 | Jensen et al. | 623/17.11 |
| 2014/0188233 A1* | 7/2014 | Mutchler et al. | 623/19.14 |

OTHER PUBLICATIONS

Denis, F. "The three column spine and its significance in the classification of acute thoracolumbar spinal injuries" Spine Nov.-Dec. 1983; 8(8):817-831.
Ozgur, Aryan et al. "Extreme Lateral Interbody Fusion (XLIF): a novel surgical technique for anterior lumbar interbody fusion" Spine J. Jul.-Aug. 2006; ; 6(4):435-43.

* cited by examiner

*Primary Examiner* — Jerry Cumberledge
*Assistant Examiner* — Tessa Matthews
(74) *Attorney, Agent, or Firm* — Gazdzinski & Associates PC

(57) ABSTRACT

Apparatus and methods for spinal the treatment of abnormal spinal stability and stenosis of the spinal canal. In one embodiment, the apparatus and methods provide treatment via decompression and/or fixation of the spinal canal. One or more implants are used to fixate the posterior column of a spinal segment compromised of the superior and inferior immediately adjacent vertebral bones. In one variant, these disclosed devices are used to fixate the posterior column of a spinal segment while another orthopedic implant is placed into the anterior column of the same spinal segment, thereby providing circumferential decompression.

36 Claims, 27 Drawing Sheets

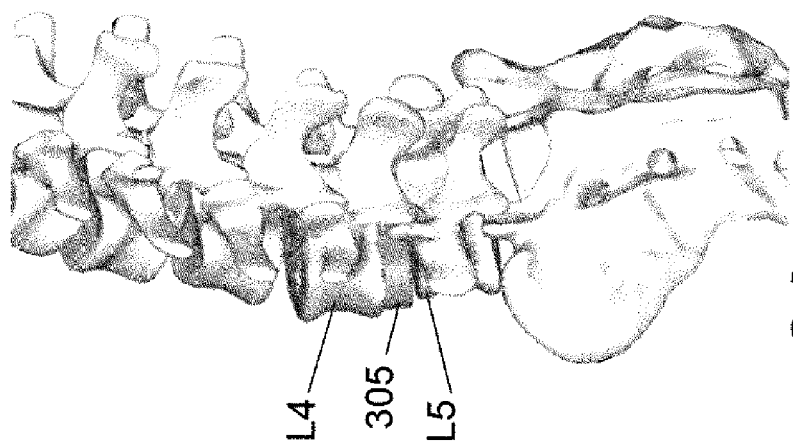

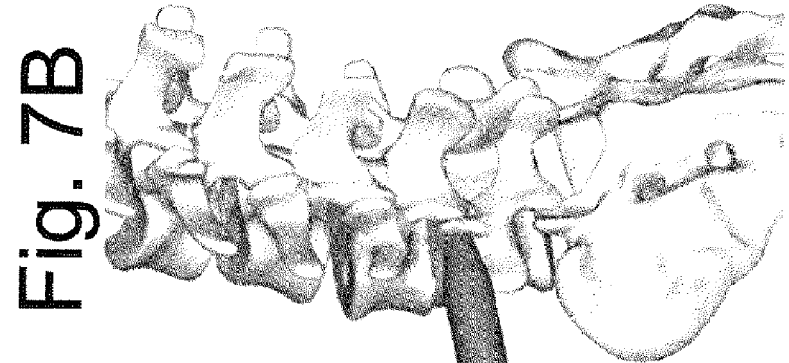
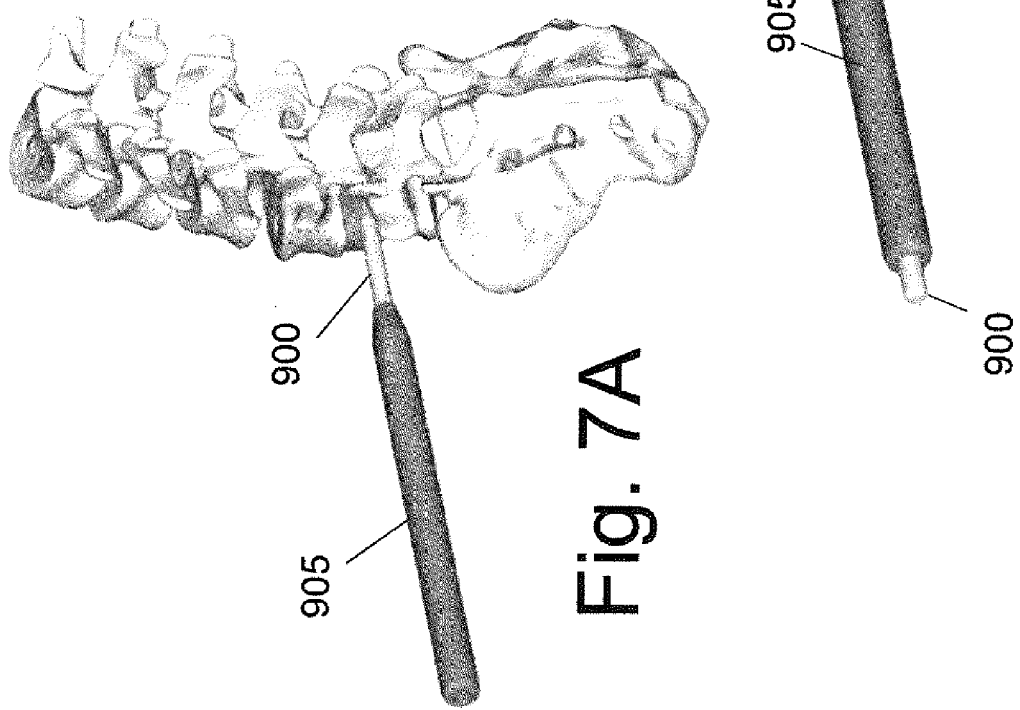

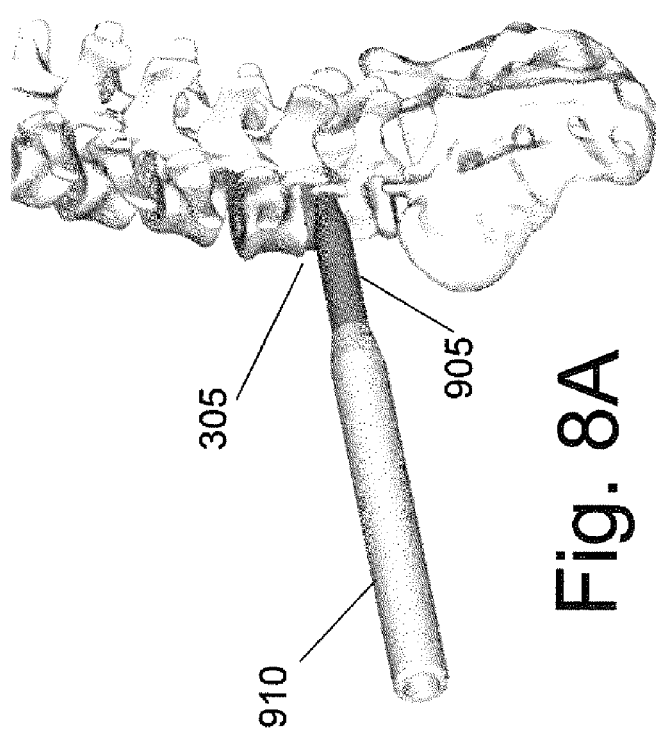

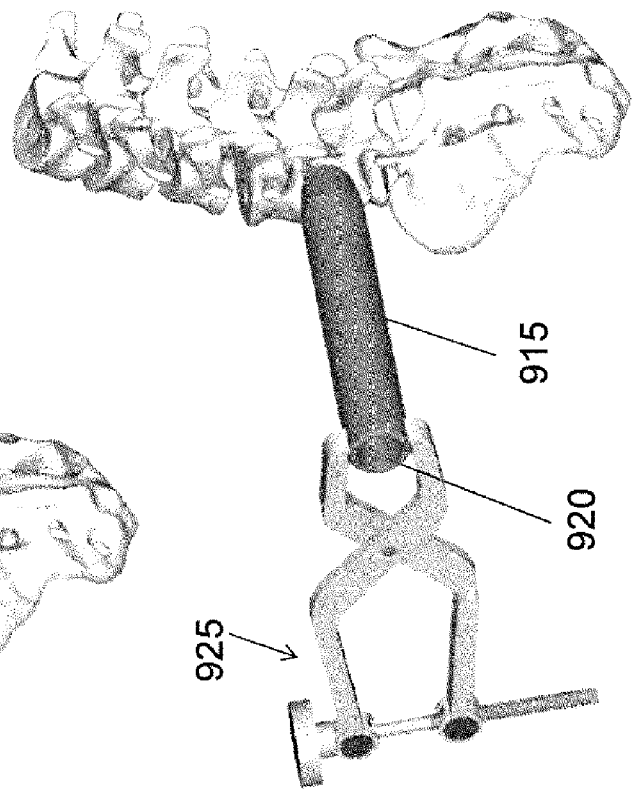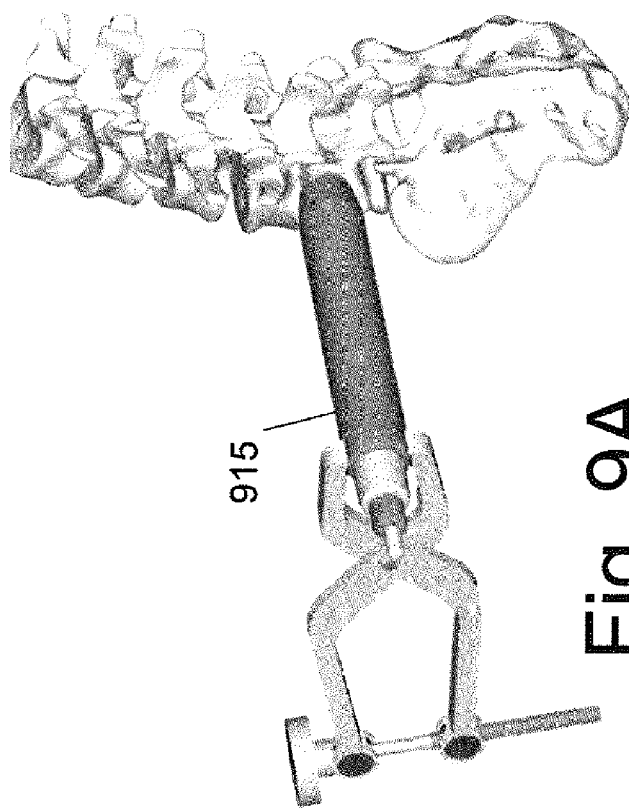

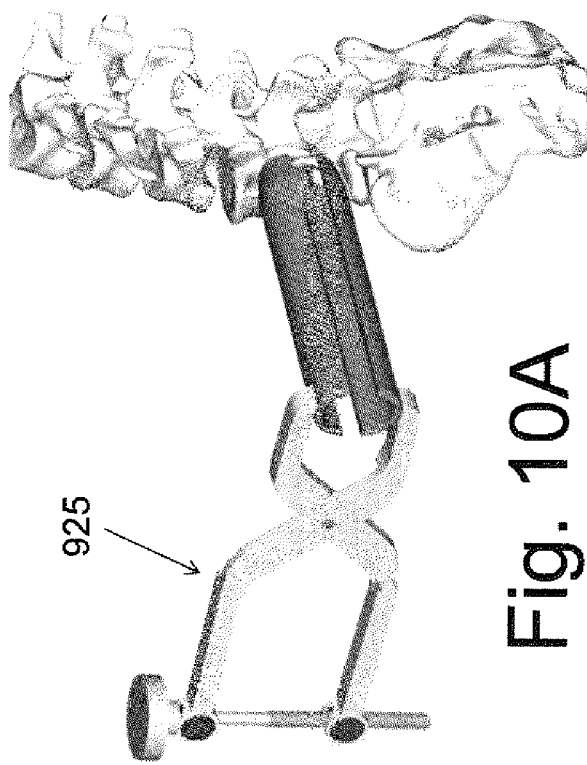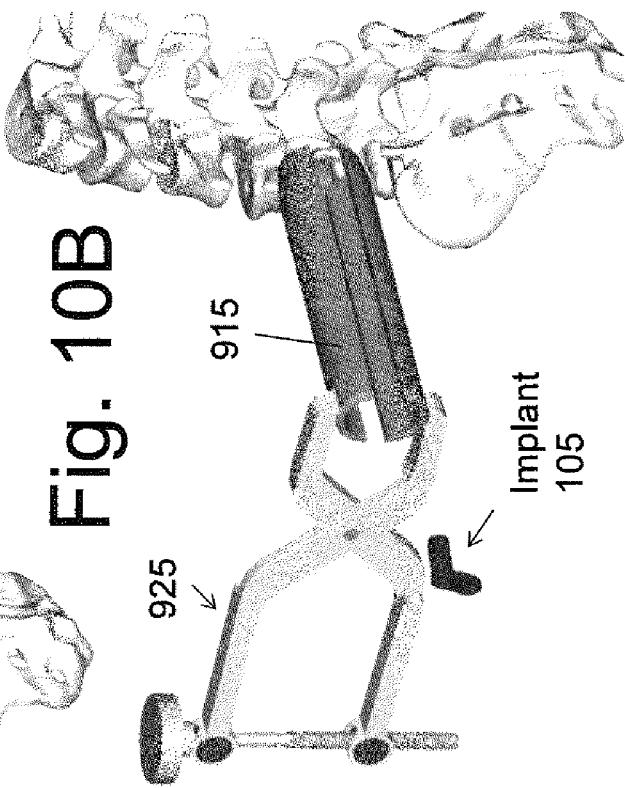

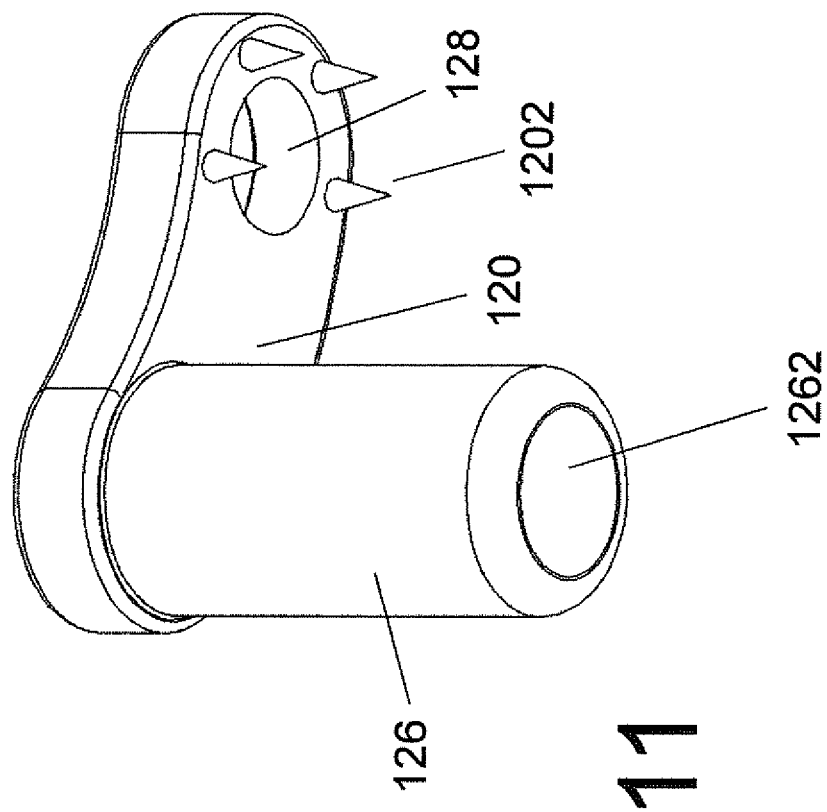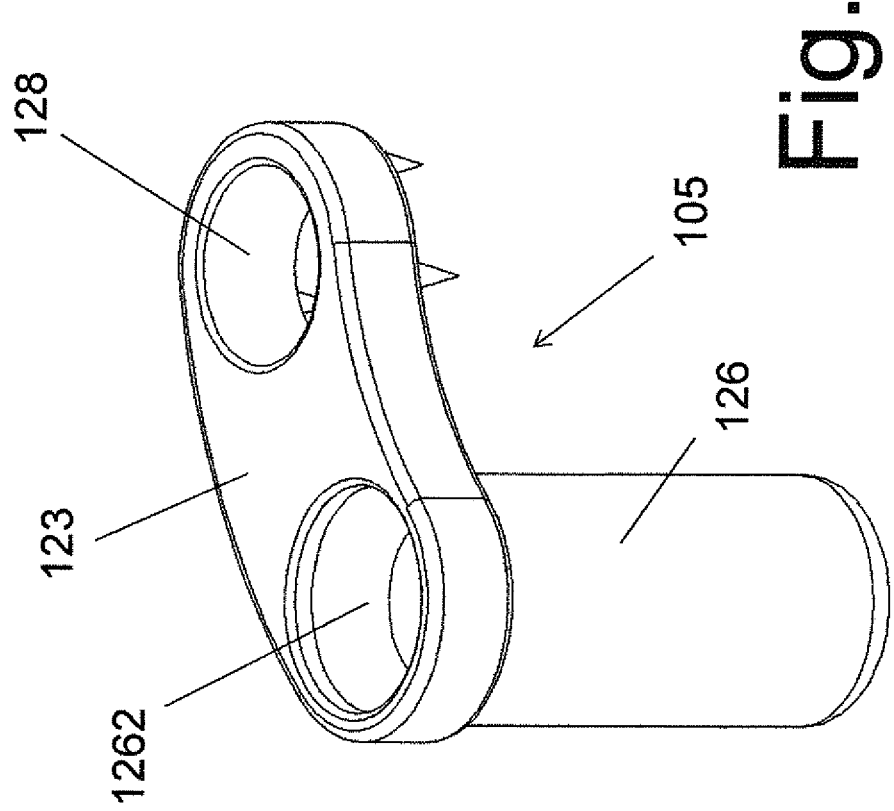
Fig. 11

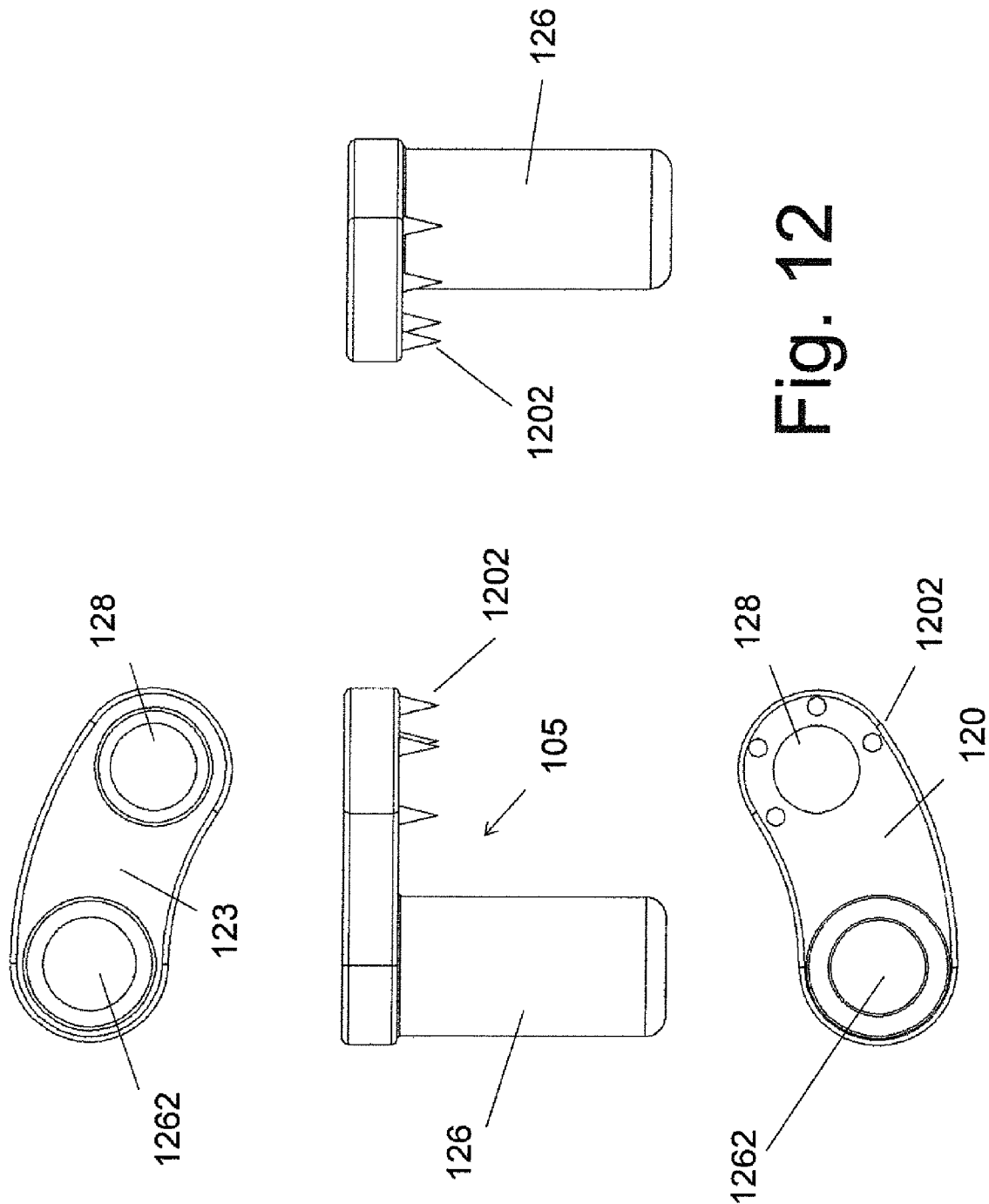

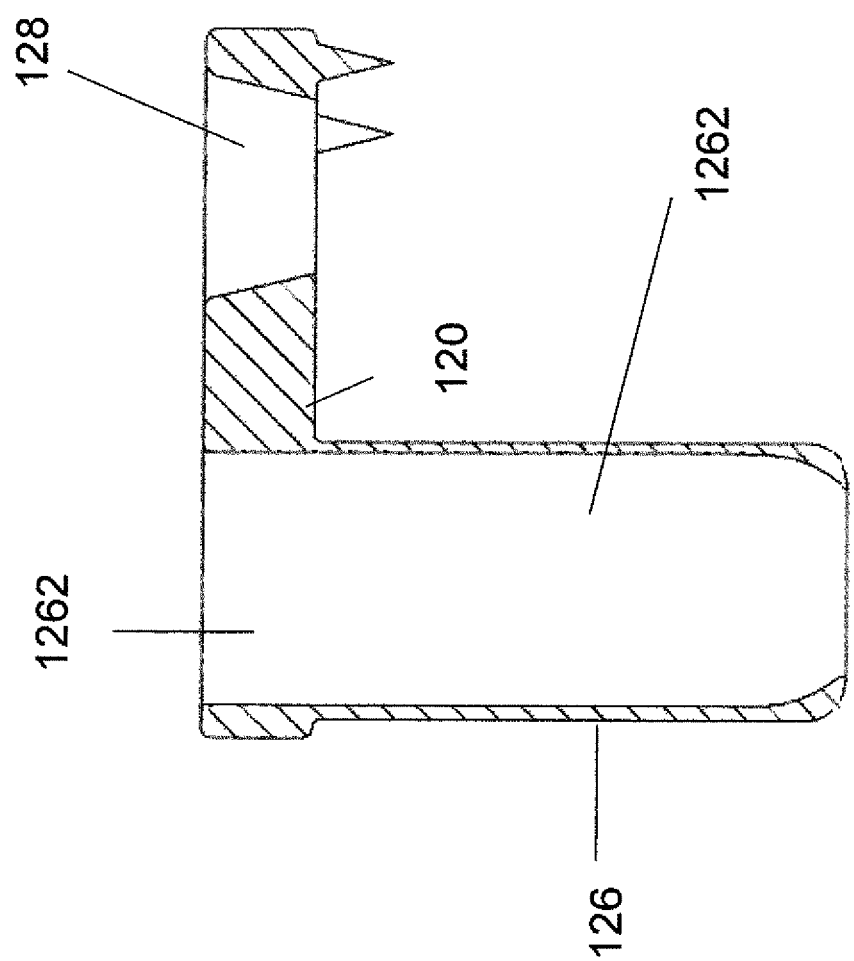

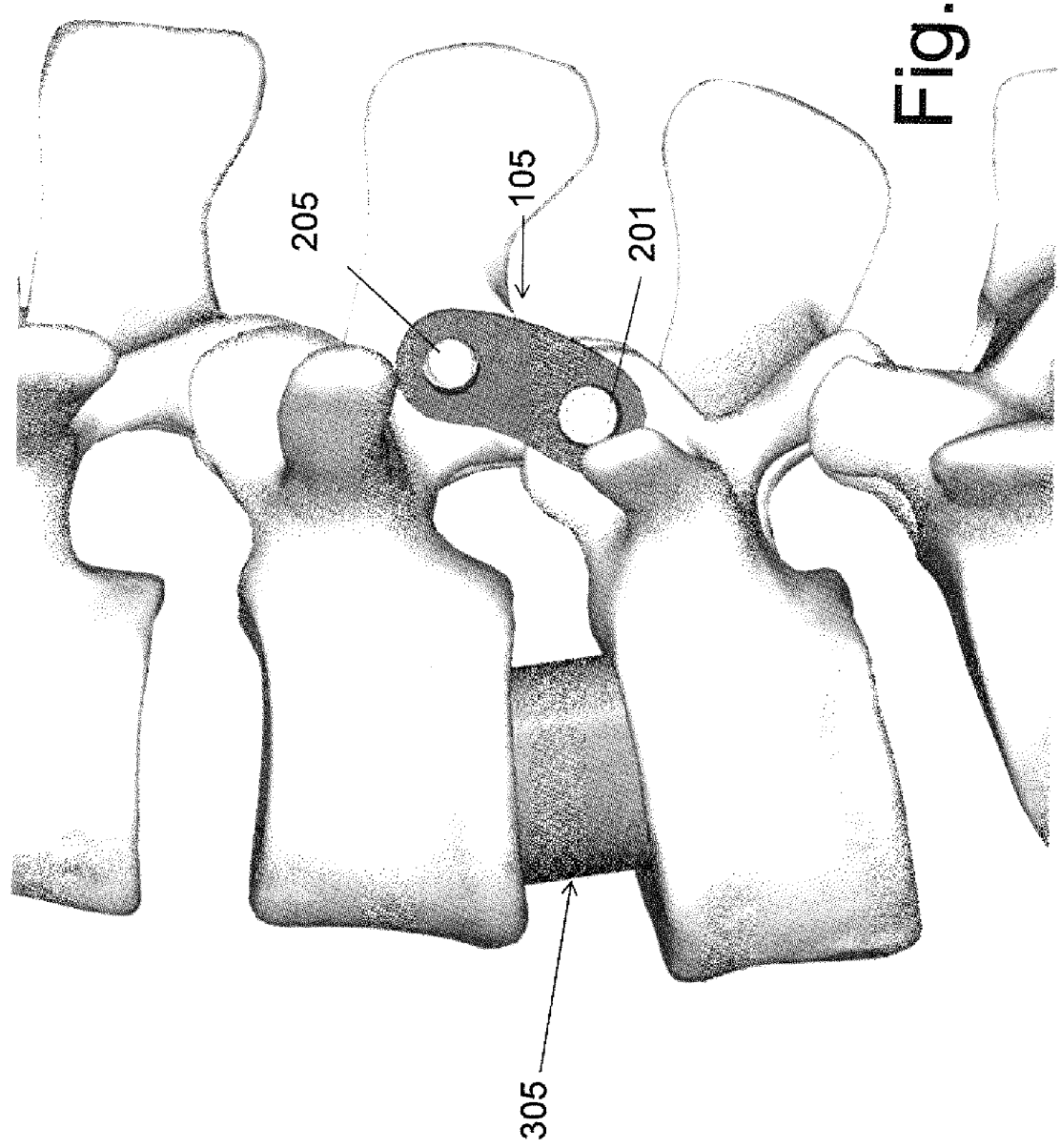

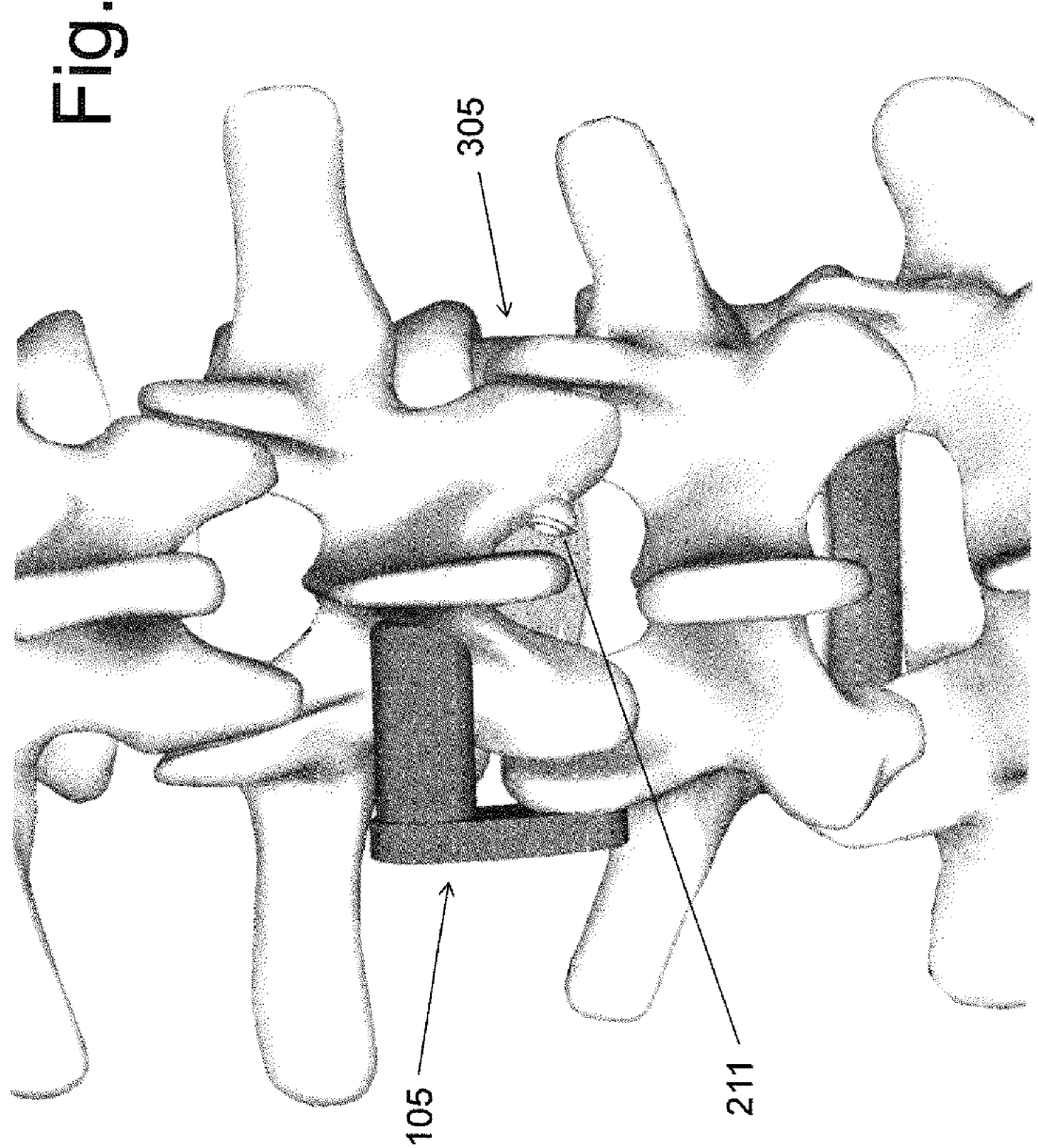

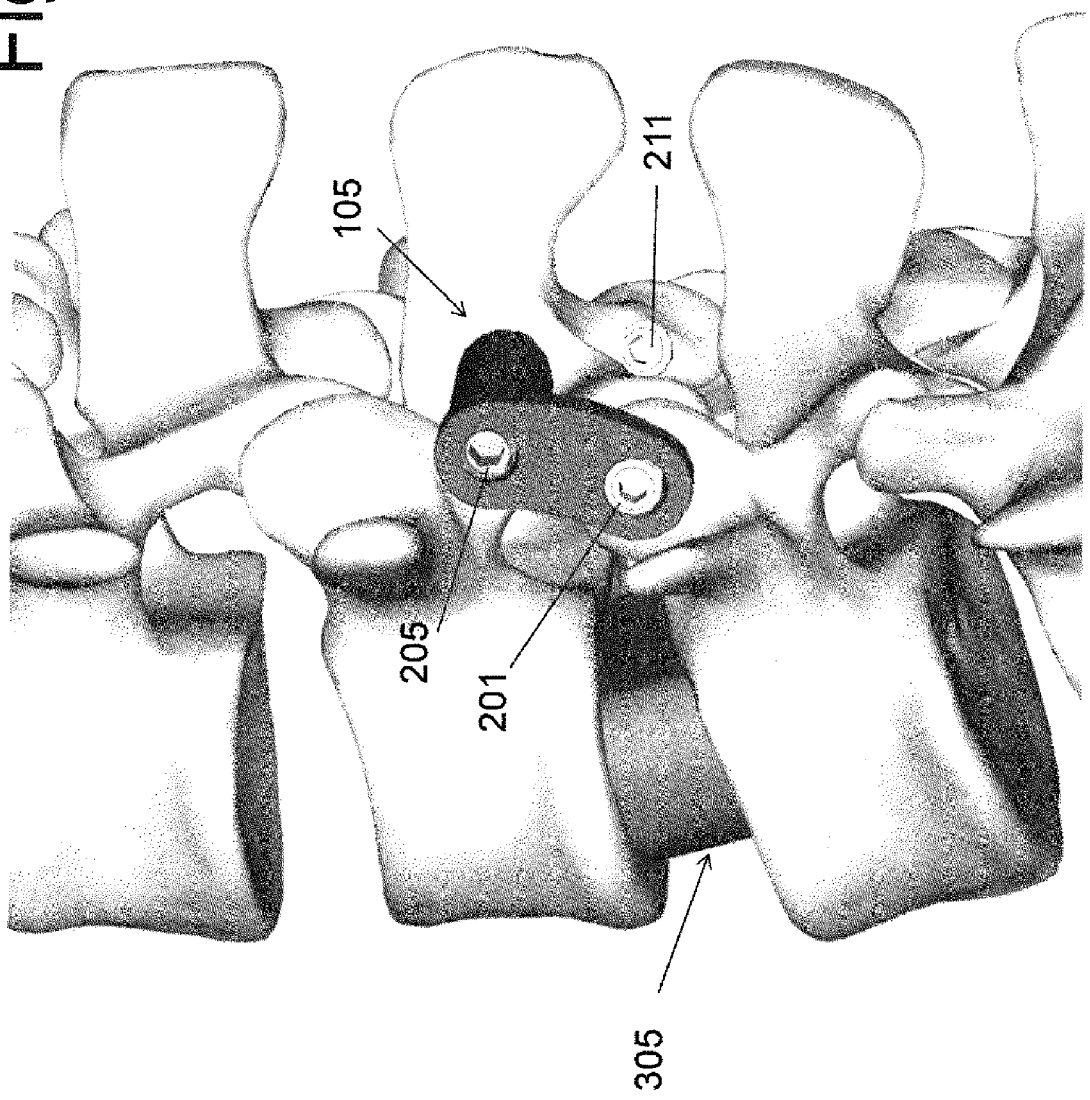

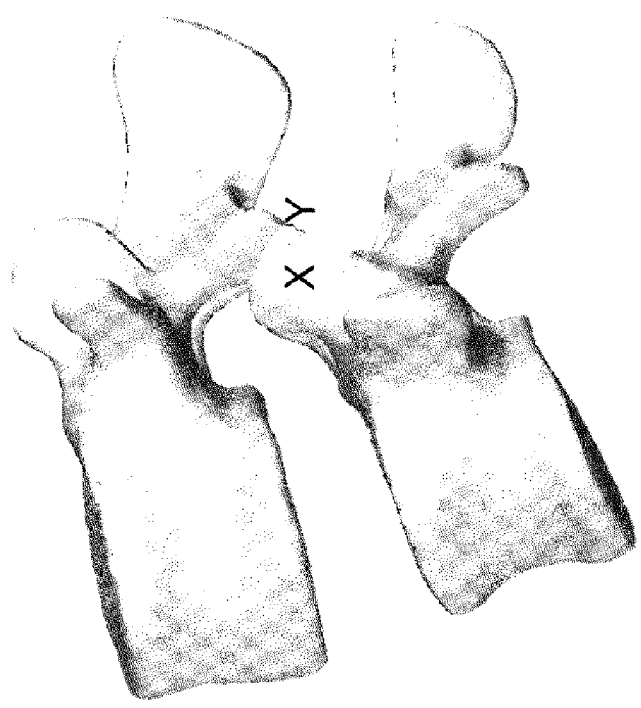
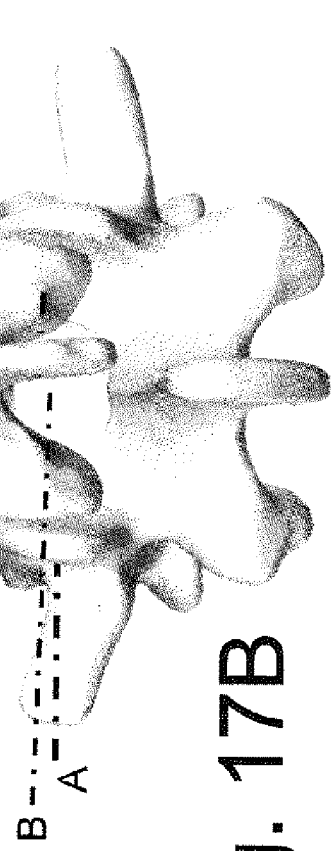
Fig. 17A
Fig. 17B

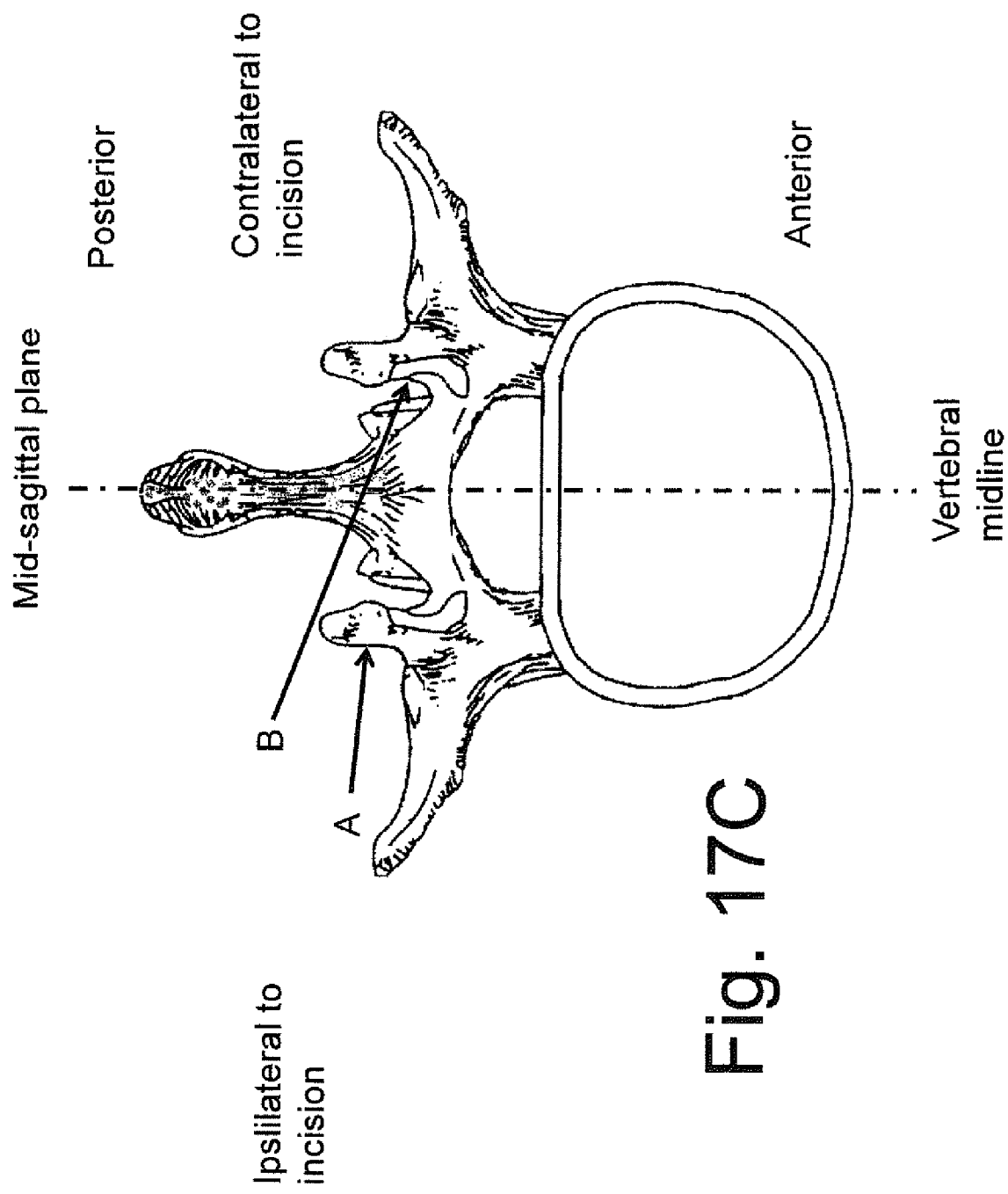

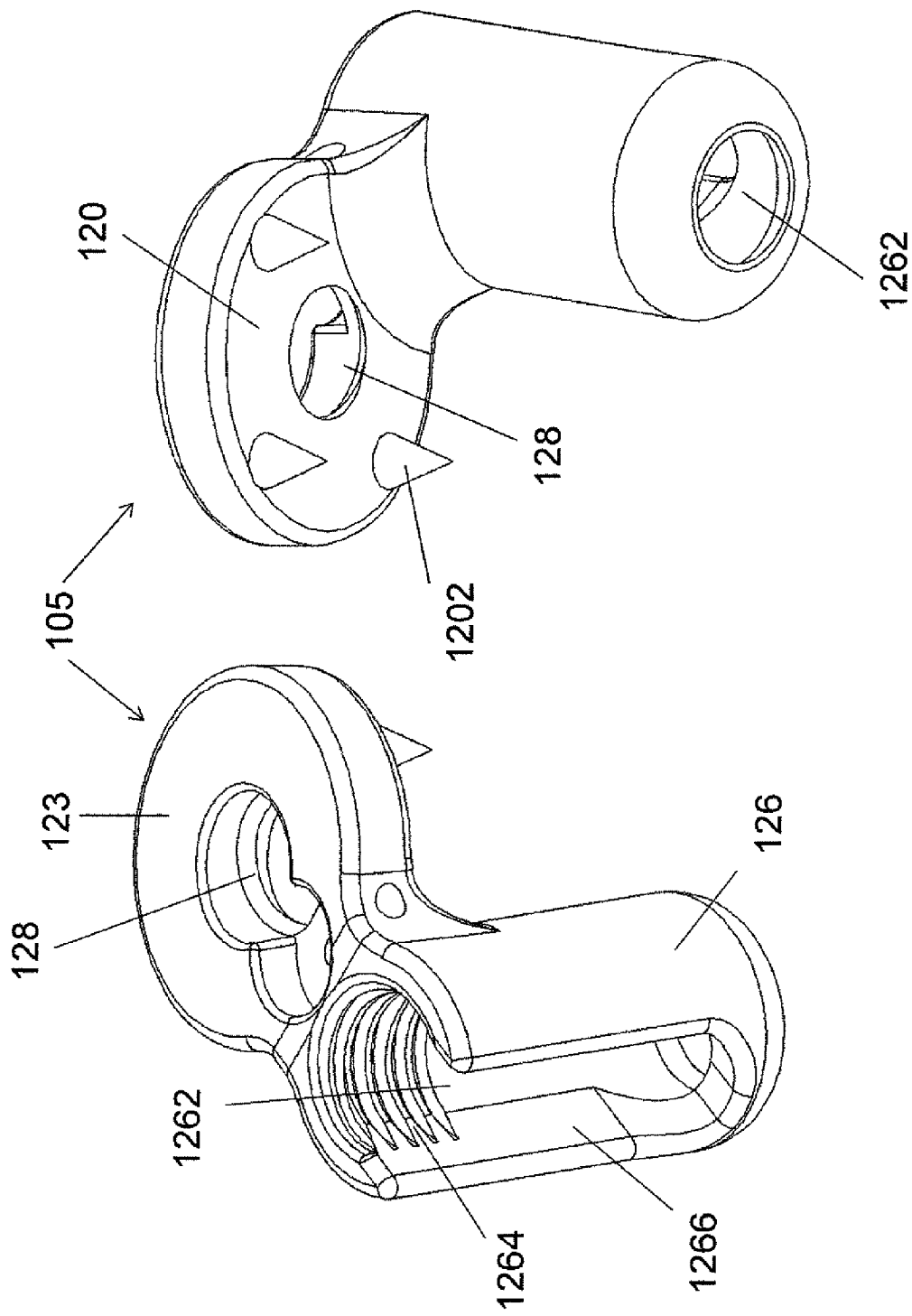

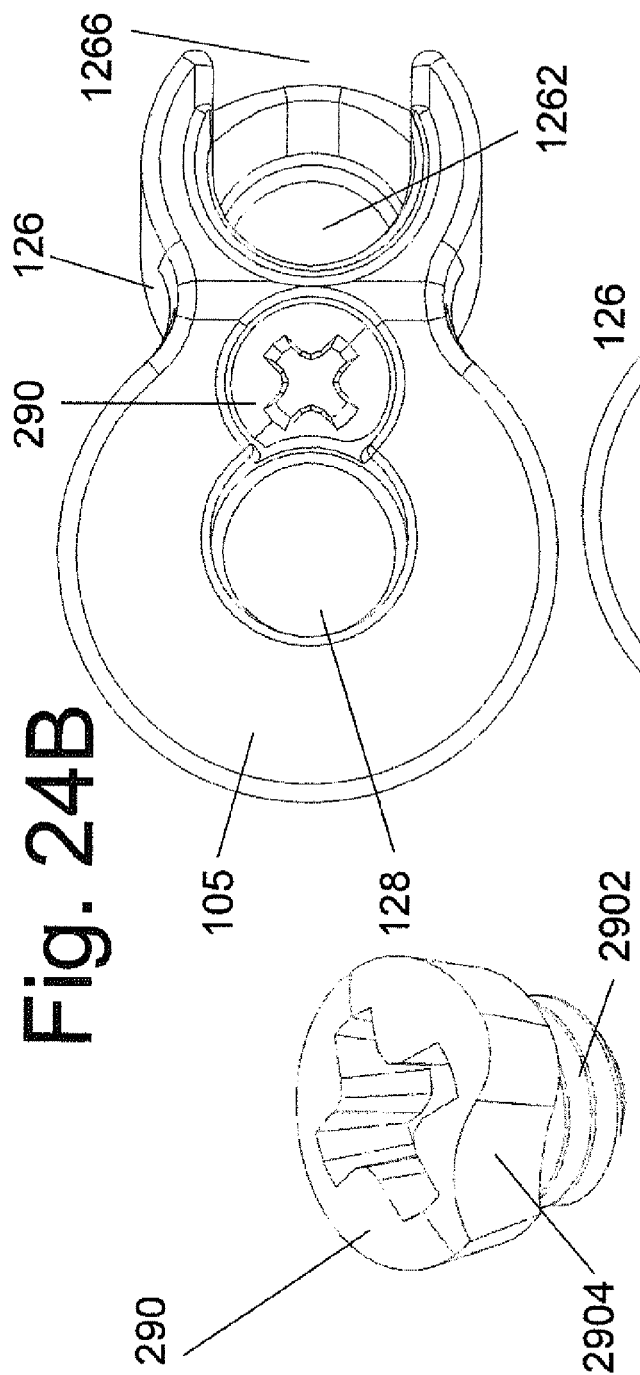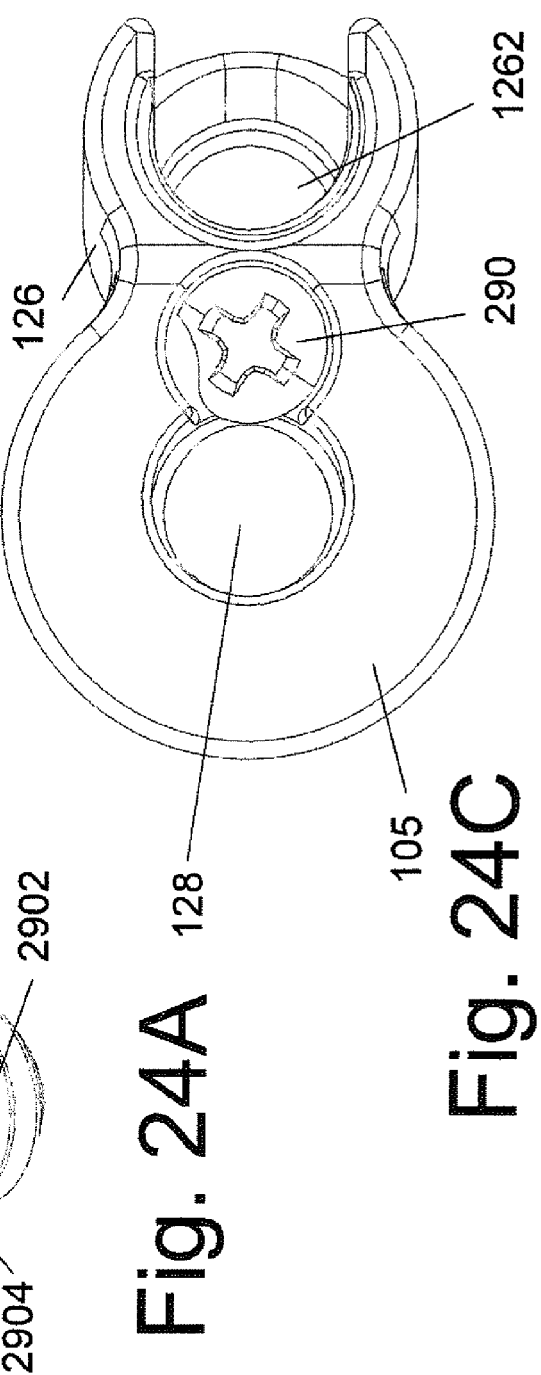
Fig. 24A
Fig. 24B
Fig. 24C

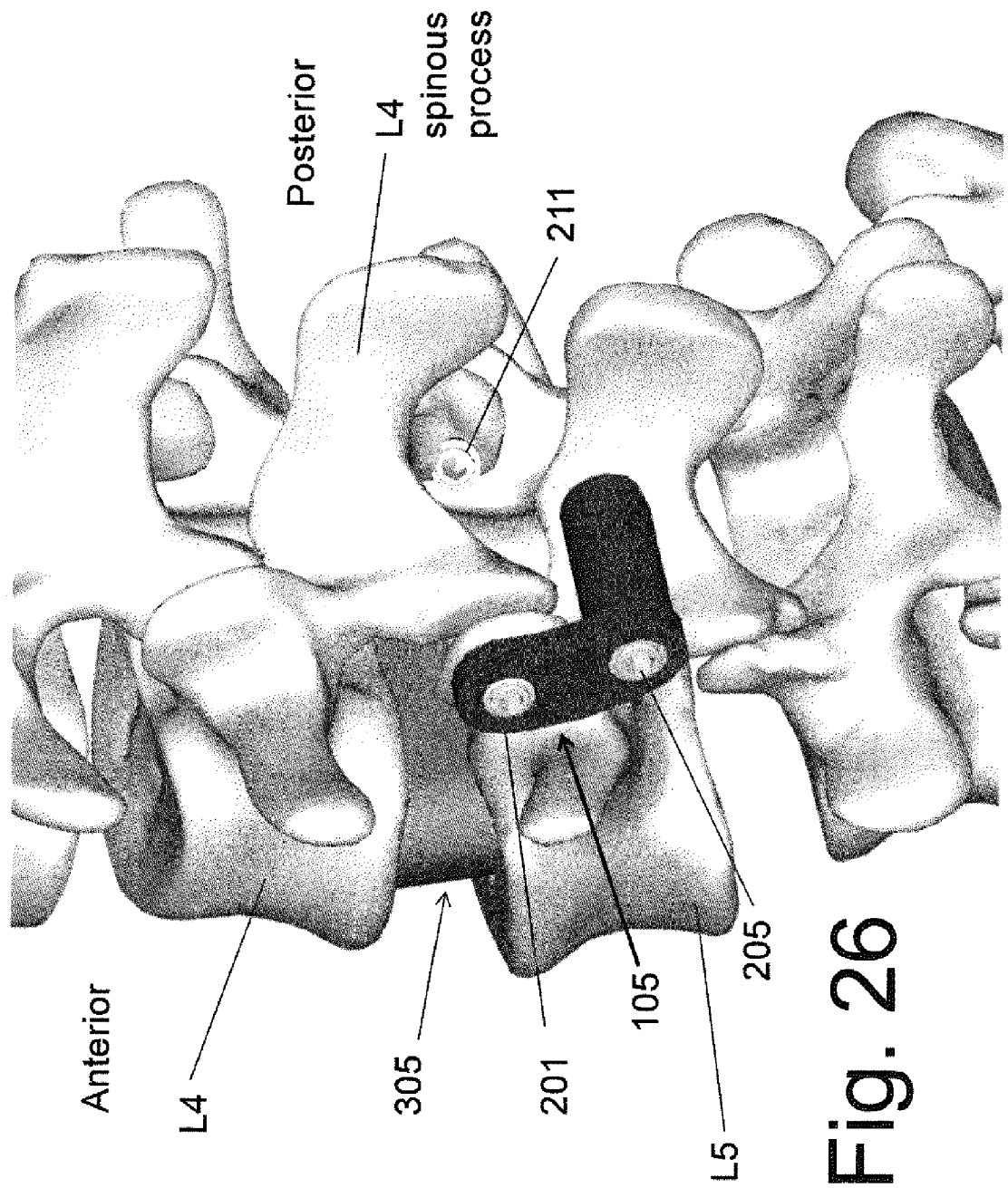

DEVICES AND METHODS FOR SPINAL STABILIZATION AND INSTRUMENTATION

PRIORITY

This application claims priority to U.S. Provisional Patent Application Ser. No. 61/743,162 filed on Aug. 28, 2012 of the same title, and to U.S. Provisional Patent Application Ser. No. 61/797,177 filed on Dec. 1, 2012 of the same title, each of which is incorporated herein by reference in its entirety.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

BACKGROUND

1. Field of the Disclosure

This disclosure relates generally to bone fixation systems. In one exemplary aspect, apparatus and methods are disclosed for implant placement so as to adjust, align and maintain the spatial relationship(s) of adjacent bones or bony fragments after e.g., surgical reconstruction of skeletal segments.

2. Description of Related Technology

Whether from degenerative disease, traumatic disruption, infection or neoplastic invasion, alteration in the anatomical relationships between the spinal vertebras can cause significant pain, deformity and disability. Spinal disease is a major health problem in the industrialized world and the surgical treatment of spinal pathology is an evolving discipline. The traditional surgical treatment of abnormal vertebral motion is the complete immobilization and bony fusion of the involved spinal segment and an extensive array of surgical techniques and implantable devices have been formulated to accomplish the treatment objective.

Regardless of the specific objectives of surgery, many surgeons employ implantable devices that maintain the desired spatial relationship(s) between adjacent vertebral bodies. The effectiveness of these devices is critically dependant on adequate fixation into the underlying bone. While screw fixation into the pedicle portion of the vertebral body has emerged as a common method of device fixation, it remains a substantial operation with multiple shortcomings.

Hence, it would be desirable to provide improved spinal fixation devices and methods of their use.

SUMMARY

The present disclosure addresses the foregoing needs by disclosing, inter alia, apparatus and methods for the treatment of abnormal spinal stability and stenosis of the spinal canal by providing decompression and/or fixation thereof.

In a first aspect, a method for bilaterial immobilization of a facet joint is disclosed. In one embodiment, the method includes implanting one or more implants to fixate the posterior column of a spinal segment compromised of the superior and inferior immediately adjacent vertebral bones.

In another embodiment, the method comprises: (i) approaching a lateral aspect of an ipsilateral facet joint, the ipsilateral facet joint comprising an inferior articulating process of a superior vertebral bone and a superior articulating process of an inferior vertebral bone, (ii) positioning a first segment of an orthopedic implant to abut a lateral side wall of the superior articulating process of the inferior vertebral bone, (iii) positioning a second segment of the orthopedic implant to extend medial to the ipsilateral facet joint, (iv) coupling a first bone fastener to the first segment of the orthopedic implant, (v) advancing the first bone fastener from a lateral aspect to a medial aspect of the ipsilateral facet joint, (vi) coupling a second bone fastener to the second segment of the orthopedic implant, and (vii) advancing the second bone fastener from a medial to a lateral aspect of a contralateral facet joint.

In yet another embodiment, the method includes: approaching a portion of an facet joint, said facet joint comprising an first articulating process of a first vertebral bone and a second articulating process of a second vertebral bone; positioning a first segment of an orthopedic implant to abut at least a portion of said second articulating process of said second vertebral bone; positioning a second segment of said orthopedic implant to extend proximate to said facet joint; coupling a first bone fastener to said first segment of said orthopedic implant; advancing said first bone fastener from a first aspect to a second aspect of said facet joint; coupling a second bone fastener to said second segment of said orthopedic implant; and advancing said second bone fastener from a first aspect to a second aspect of a second facet joint.

In a second aspect, a method of providing decompression of spinal stenosis is disclosed. In one embodiment, the method comprises rigidly fixating the superior articulating process (SAP) of an inferior vertebral bone with the bony segment of an immediately superior vertebral bone. In another embodiment, the method comprises: percutaneously placing an implant such that the superior articulating process (SAP) of the inferior vertebral bone and the superior articulating process (SAP) of the immediately superior vertebral bone are retained in the distracted position.

In a third aspect, an orthopedic implant is disclosed. In one embodiment, the implant includes a body configured to abut a lateral side wall of the superior articulating process of the inferior vertebral bone, and extend medial to the ipsilateral facet joint, and two bone fasteners configured to be accepted within respective portions of the body. The first of the two bone fasteners is configured to be advanced from a lateral aspect to a medial aspect of the ipsilateral facet joint. The second of the two bone fasteners is configured to be advanced from a medial to a lateral aspect of a contralateral facet joint.

In a fourth aspect, a placement instrument for implanting an implant within a subject spine is disclosed. In one embodiment, the placement instrument includes a first tissue dilator configured to be placed through a lateral corridor to a target implant location, one or more second tissue dilators of greater diameter than the first tissue dilator and configured to be placed over the first tissue dilator, and a distraction device configured to be placed over the first and the one or more second tissue dilators. The distraction device is further configured to be distracted such that the first and the one or more second tissue dilators may be removed and the implant implanted at the target implant location.

The details of one or more embodiments are set forth in the accompanying drawings and description below. Other features, objects, and advantages will be apparent from the following description, the accompanying drawings and from the claims.

BRIEF DESCRIPTION OF THE DRAWINGS

FIG. 6A is a side perspective view of a subject spine having an exemplary implant positioned within the L4/L5 disc space.

FIG. 6B is a side perspective view of a subject spine having an exemplary cylindrical tissue dilator placed between L4 and L5.

FIGS. 7A-7B are side perspective views of a subject spine having a second exemplary tissue dilator placed over the tissue dilator of FIG. 6B.

FIGS. 8A-8B are side perspective views of a subject spine having a third tissue dilator placed over the tissue dilator of FIGS. 7A-7B.

FIG. 9A is a side perspective view of a subject spine having exemplary tubular half-receptacles placed over the tissue dilator of FIGS. 8A-8B.

FIG. 9B is a side perspective view of a subject spine having exemplary tubular half-receptacles in position and having the tissue dilators of FIGS. 6B, 7A-7B, and 8A-8B removed.

FIGS. 10A-10B are side perspective views of a subject spine having exemplary tubular half-receptacles in a distracted position and prepared for implantation of an exemplary implant.

FIG. 11 are side perspective views of an exemplary implant for use with the present disclosure.

FIG. 12 are orthogonal views of the exemplary implant of FIG. 11.

FIG. 13 is a sectional view of the exemplary implant of FIG. 11.

FIG. 14 is a lateral perspective view of a subject spine having an exemplary implant positioned therein according to the present disclosure.

FIG. 15 is a posterior view of a subject spine having an exemplary implant positioned therein according to the present disclosure.

FIG. 16 is an oblique view of a subject spine having an exemplary implant positioned therein according to the present disclosure.

FIG. 17A is a lateral view of a subject spine having an exemplary screw advanced therein according to the present disclosure.

FIG. 17B is a posterior view of a subject spine illustrating an exemplary trajectory for advancement of the exemplary screw of FIG. 17A.

FIG. 17C is an axial plane view of a subject spine illustrating an exemplary trajectory for advancement of the exemplary screw of FIG. 17A.

FIG. 23 is multiple perspective views of a portion of the assembled implant of FIG. 20.

FIG. 24A is a side perspective view of a head portion of an exemplary screw for use with the present disclosure.

FIGS. 24B and 24C are top views illustrating rotation of the exemplary screw of FIG. 24A into an immobilized position.

FIG. 26 is an oblique view of a subject spine illustrating an attachment of an exemplary implant as in FIG. 25.

Figure 1:
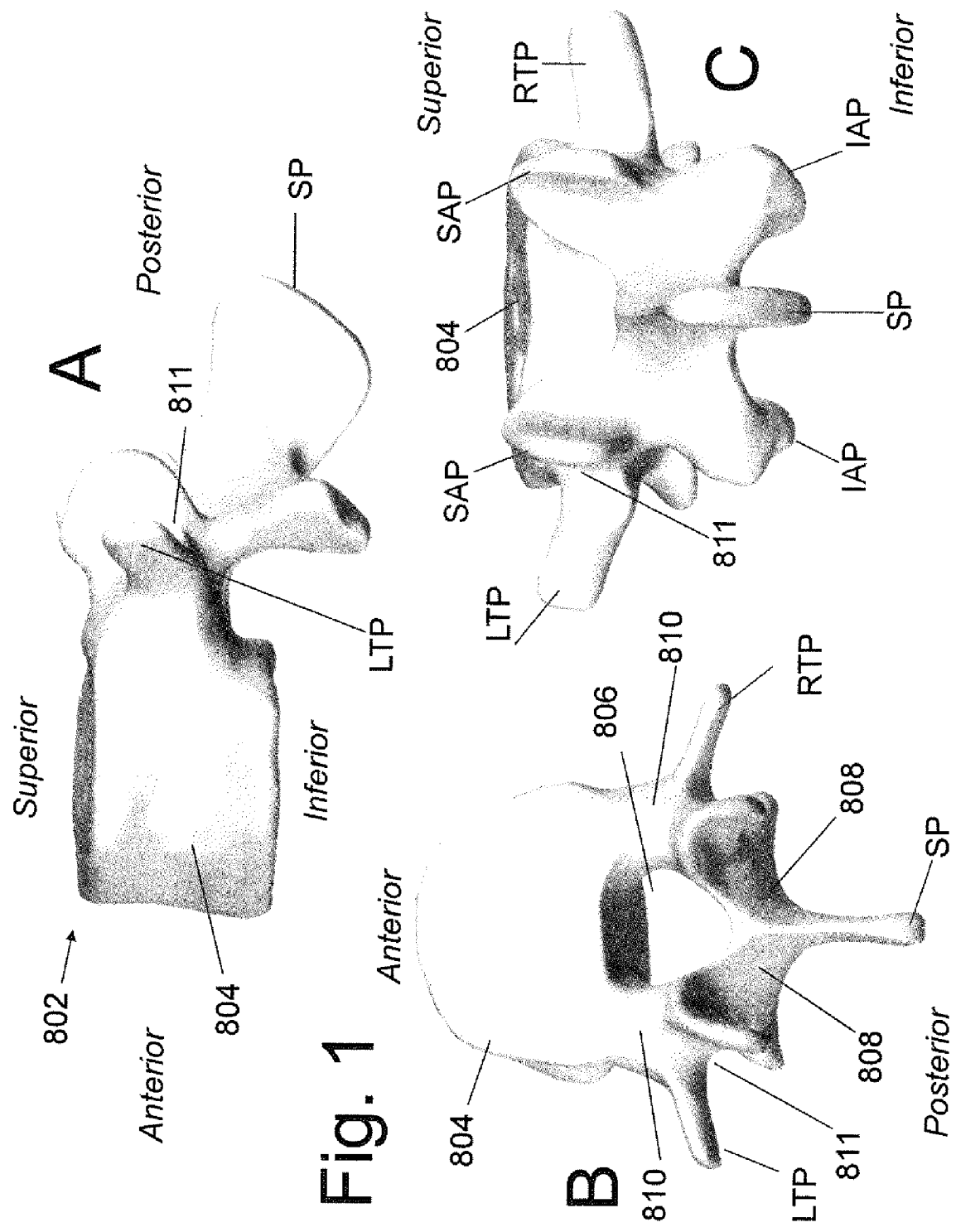
FIG. 1 provides multiple views of an exemplary spinal vertebral bone.

All Figures © Copyright 2013. Samy Abdou. All rights reserved.

Overview

In one aspect, improved apparatus and methods for spinal the treatment of abnormal spinal stability and stenosis of the spinal canal by providing decompression and/or fixation thereof are disclosed. In one exemplary implementation, one or more implants are used to fixate the posterior column of a spinal segment compromised of the superior and inferior immediately adjacent vertebral bones. In one variant, these disclosed devices are used to fixate the posterior column of a spinal segment while another orthopedic implant is placed into the anterior column of the same spinal segment.

Exemplary methods for implantation are also disclosed. In one particular embodiment, the implant is percutaneously placed and used to provide decompression of spinal stenosis by retaining the superior articulating process (SAP) of the inferior vertebral bone and the superior articulating process (SAP) of the immediately superior vertebral bone in the distracted position.

The exemplary embodiments of the herein-described methods and devices provide circumferential decompression of the spinal canal via implantation of an anterior and a posterior implant. Specifically, in one particular embodiment, an anterior column implant is used to distract the implanted disc space from a pre-implantation vertical disc space height to the greater vertical disc space height after implantation, and posterior column implant is used to simultaneously distract the posterior column of the implanted FSU. In this manner, spinal canal is decompressed circumferentially—anteriorly by the anterior implant and posteriorly by the posterior implant.

DETAILED DESCRIPTION

In order to promote an understanding of the principals of the disclosure, reference is made to the drawings and the embodiments illustrated therein. Nevertheless, it is understood that the drawings are illustrative and no limitation of the scope of the claims is thereby intended. Any such alterations and further modifications in the illustrated embodiments, and any such further applications of the principles of the disclosed devices as illustrated herein are contemplated as would normally occur to one of ordinary skill in the art.

Described herein are devices, systems and methods for the treatment of abnormal spinal stability and stenosis of the spinal canal. In an embodiment, one or more implants are used to fixate the posterior column of a spinal segment compromised of the superior and inferior immediately adjacent vertebral bones. The disclosed devices may be used alone or implanted into the spinal segment in conjunction with other orthopedic implants. In an exemplary embodiment, these disclosed devices are used to fixate the posterior column of a spinal segment while another orthopedic implant is placed into the anterior column of the same spinal segment. The anterior column implant is installed in the spinal column using a lateral or an anterior approach to the anterior column (these operations are collectively known as ALIF, XLIF, DLIF and the like). In one particular embodiment, the anterior column implant is implanted into the subject first. However, it is appreciated that either the anterior implant or the posterior column implant may be placed first into the subject.

Posterior fixation employs a device and method to rigidly fixate the superior articulating process (SAP) of an inferior vertebral bone with the bony segment of an immediately superior vertebral bone. In one particular embodiment of device use, the implant is percutaneously placed and used to provide decompression of spinal stenosis by retaining the superior articulating process (SAP) of the inferior vertebral bone and the superior articulating process (SAP) of the immediately superior vertebral bone in the distracted position.

In one embodiment of a method of device use, both anterior and posterior implants may be placed through a single lateral skin incision or two immediately adjacent skin incisions. Further, this method provides circumferential (i.e., anterior and posterior) expansion and decompression of the spinal canal so as to treat spinal stenosis though simultaneous anterior and posterior decompression of the spinal canal. That is, the anterior column implant is used to distract the implanted disc space from a pre-implantation vertical disc space height to the greater vertical disc space height after implantation. (The term disc space height is well known to those of ordinary skill in the art and generally refers to the vertical distance of the disc space as measured from the inferior bone surface of the vertebral bone forming the superior border of the disc space to the superior bone surface of the of the vertebral bone forming the inferior border of the disc space.) The posterior column implant is used to simultaneously distract the posterior column of the implanted FSU. In this way, the spinal canal is decompressed circumferentially—anteriorly by the anterior implant and posteriorly by the posterior implant. In application within a lateral approach to the spinal column, the method allows the spinal canal to be circumferentially decompressed by a single (or two immediately adjacent) incision(s).

As used herein, the anterior column generally designates a portion of the vertebral body and/or Functional Spinal Unit (FSU) that is situated anterior to the posterior longitudinal ligament. Thus, its use in this application encompasses both the anterior and middle column of Denis (see "The three column spine and its significance in the classification of acute thoracolumbar spinal injuries." Denis, F. *Spine* 1983 November-December; 8(8):817-31, which is incorporated by reference in its entirety.) The illustrations and definitions of anatomical structures are known to those of ordinary skill in the art. They are described in more detail in *Atlas of Human Anatomy*, by Frank Netter, *third edition, Icon Learning Systems*, Teterboro, N.J. The text is hereby incorporated by reference in its entirety. It should be appreciated that the directional language and terms regarding orientation such as upper, lower, upward, downward etc. are used throughout merely for convenience of description and are not intended to be limiting.

FIG. 1 shows various diagrammatic representations of a spinal vertebral bone 802 in multiple views. For clarity of illustration, the vertebral bone of FIG. 1 and those of other illustrations disclosed herein are represented schematically and it should be appreciated that actual vertebral bodies may include anatomical details that are not shown in these figures. Further, it is understood that the vertebral bones at a given level of the spinal column of a human or animal subject contain anatomical features that may not be present at other levels of the same spinal column. The illustrated vertebral bones are intended to generically represent vertebral bones at any spinal level without limitation. The disclosed devices and methods may be applied at any applicable spinal level.

Vertebral bone 802 contains an anteriorly-placed vertebral body 804, a centrally placed spinal canal 806 and posteriorly-placed lamina 808. The pedicle segments 810 of vertebral bone 802 form the lateral aspect of the spinal canal 806 and connect the laminas 808 to the vertebral body 804. The spinal canal 806 contains neural structures such as the spinal cord and/or nerves. A midline protrusion termed the spinous process SP extends posteriorly from the medial aspect of laminas 808. A protrusion extends laterally from each side of the posterior aspect of the vertebral bone 802 and is termed the transverse process TP. A right transverse process RTP extends to the right and a left transverse process LTP extends to the left. A superior protrusion extends superiorly above the lamina 808 on each side of the vertebral midline and is termed the superior articulating process SAP. An inferior protrusion extends inferiorly below the lamina 808 on each side of the vertebral midline and is termed the inferior articulating process IAP. Note that the posterior aspect of the pedicle 810 can be accessed at an indentation 811 in the vertebral bone 802 between the lateral aspect of the SAP and the medial aspect of the transverse process TP. In surgery, it can be common practice to anchor a bone fastener into the pedicle portion 810 of a vertebral bone 802 by inserting the fastener through indentation 811 and into the underlying pedicle 810.

Figure 2:
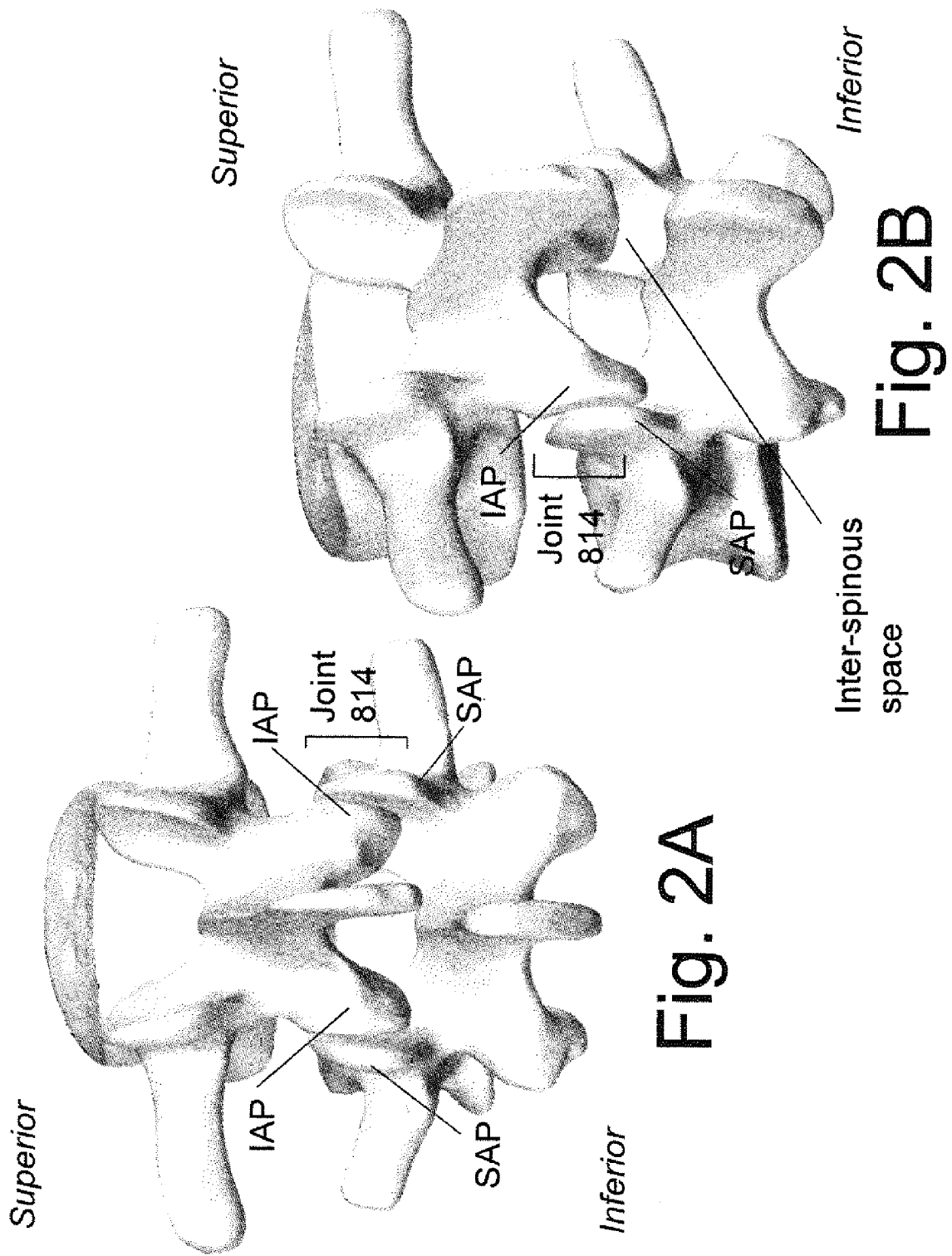
FIG. 2A is a view of an exemplary functional spinal unit (FSU), which includes two adjacent vertebrae and the intervertebral disc between them illustrating a posterior surface of the adjacent vertebrae and the articulations between them.
FIG. 2B is an oblique view of the exemplary FSU of FIG. 2A.

FIGS. 2A and 2B illustrate a (Functional Spinal Unit) FSU, which includes two adjacent vertebrae and the intervertebral disc between them. The intervertebral disc resides between the inferior surface of the upper vertebral body and the superior surface of the lower vertebral body, although it is not specifically shown in the figures. FIG. 2A shows the posterior surface of the adjacent vertebrae and the articulations between them. FIG. 2B shows an oblique view. The FSU contains a three joint complex between the two vertebral bones, with the intervertebral disc comprising the anterior joint. The posterior joints include a facet joint 814 on each side of the midline, wherein the facet joint 814 contains the articulation between the IAP of the superior vertebral bone and the SAP of the inferior bone.

The interspinous space is generally defined as the space immediately between the spinous processes of a superior vertebral bone and the spinous process of an immediately adjacent inferior vertebral bone. The interspinous space is limited anteriorly by the spinal canal 806 and posteriorly by the posterior tip of the spinous processes. The right lateral aspect of the interspinous space is limited by the right lateral side of the spinous processes whereas the left lateral aspect of the interspinous space is limited by the left lateral side of the spinous processes. Note that the spinous processes of adjacent vertebral bones may be rotated in the axial plane relative to one another because of biological and/or individual variation (schematically shown in FIG. 2). The interspinous space would continue to be defined as residing between the spinous processes of the superior and inferior vertebral bones.

Figure 3:
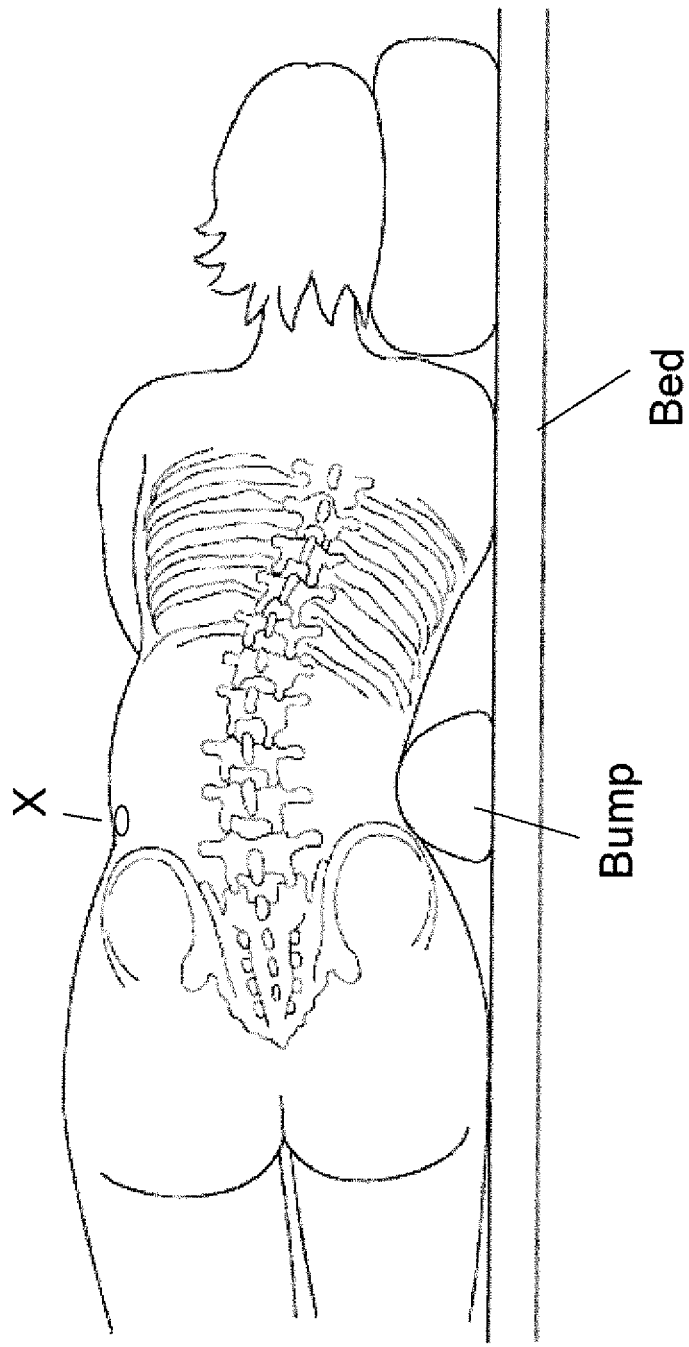
FIG. 3 is a schematic representation of a patient placed in a lateral decubitus.

As mentioned above, some device embodiments perform a spacing function wherein they distract and separate the ipsilateral superior articulating processes (SAPs) of each of the inferior and superior vertebral bones of the functional spinal unit to be fixated. It also fixates and immobilizes the SAPs of these two adjacent vertebral bones. These devices can be implanted using a lateral approach with the patient in the lateral decubitus position. (An example of a patient placed in the lateral decubitus in shown in FIG. 3.) While the patient is positioned in the lateral decubitus position, an anterior column implant may be placed through a skin incision at or about "X". The same or a closely adjacent skin incision is also used to place the posterior column implant.

It is contemplated that the fixation devices described herein are particularly adapted to be placed through a lateral surgical approach to the spine that starts with a surgical incision within the patient's flank (i.e., side aspect of the abdominal cavity). The fixation devices described herein are also particularly adapted for use in stabilizing the posterior aspect of a spinal segment when a second orthopedic implant is implanted into the disc space of that segment using a lateral, or flank, approach to the disc space. While the lateral approach is employed in the above-described method of use, the implantation procedure of the device is by no means limited to a lateral approach to the interspinous space. That is, it is appreciated that the fixation devices described herein may be used with any surgical approach to the posterior aspect of the spine and the disclosed fixation devices can be positioned in the spine using any appropriate surgical method and/or surgical corridor.

Figure 4:
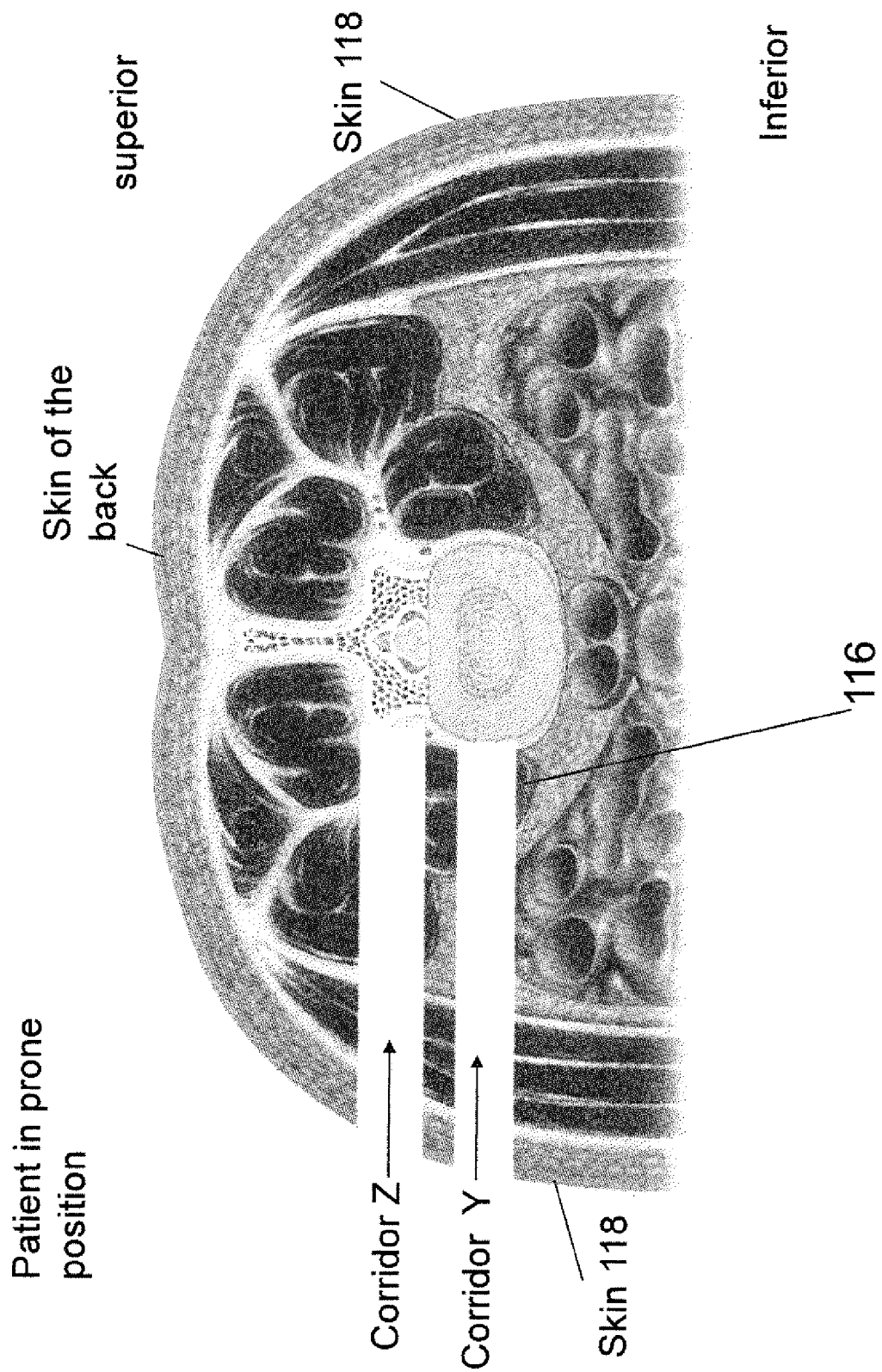
FIG. 4 is a cross sectional view of the torso at the level of the lumbar spine illustrating a flank approach for use with the present disclosure.

As noted, the fixation devices may be implanted into the lumbar spine using a flank incision and a lateral approach. The spinal level of desired device implantation can be localized under X-ray guidance. Referring to FIG. 4, a skin incision can be placed in the flank at the approximate cephalad-caudal level of the implantation site on the spine. FIG. 4 illustrates a cross sectional view of the torso at the level of the lumbar spine. For clarity of illustration, the contents are represented schematically and those skilled in the art will appreciate that an actual cross section of the human torso may include anatomical details not shown in FIG. 4.

Figure 5:
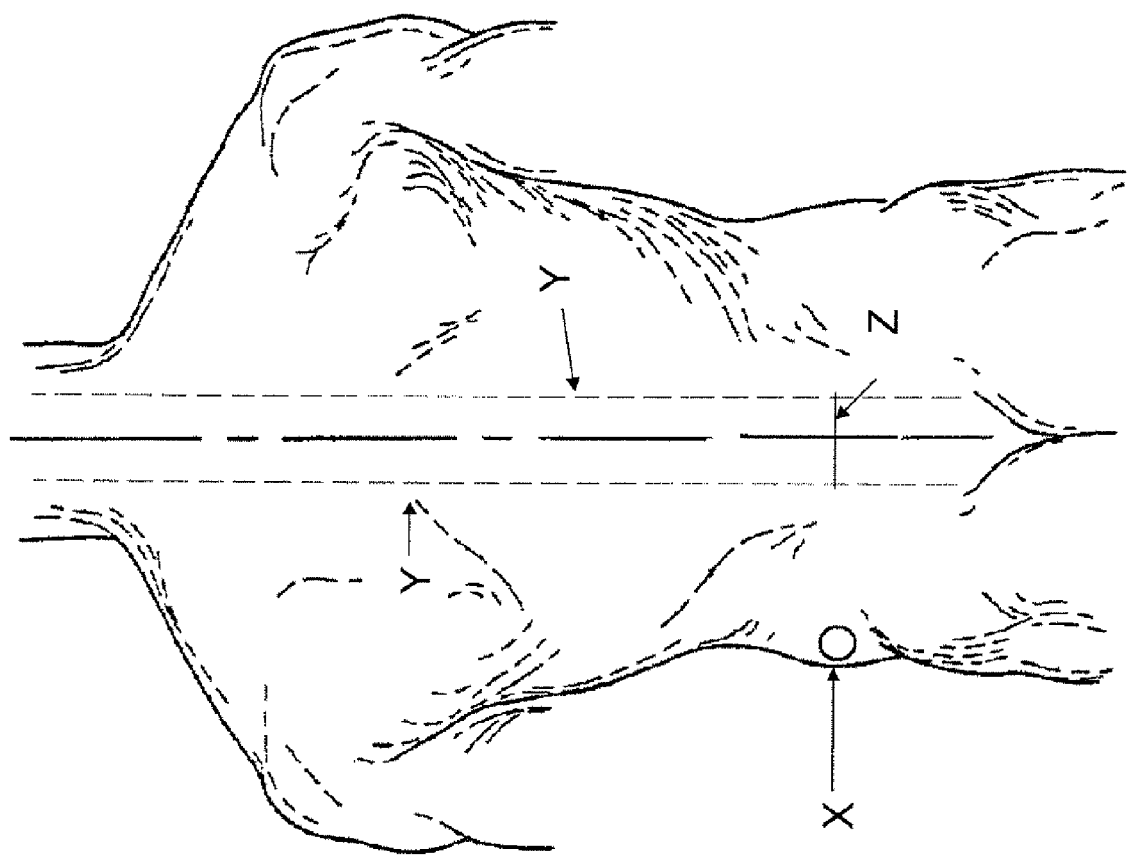
FIG. 5 is a schematic representation of the posterior aspect of a patient.

In preparation for percutaneous placement of the implant into a spinal level, the patient can be, but is not necessarily, placed in a prone or lateral decubitus position. (An example of a patient placed in a lateral decubitus in shown in FIG. 3.) The level of the spine that is to be implanted can be localized on X-ray in at least one plane. After the customary sterile preparation of the operative site, the surgeon can localize an incision point on the skin that is substantially directly lateral to the spinal segment that is to be implanted. FIG. 5 shows a schematic representation of the posterior aspect of a patient. Lines Y approximate the lateral extent of the transverse processes of the spinal column. Assuming that the spinal level to be accessed is at line Z, the surgeon can make an incision at or about circle X.

A lateral corridor "Y" (FIG. 4) can be made from the flank, through the psoas muscle 116 and onto the lateral aspect of the disc space at the spinal level to be implanted. An implant can be placed through the corridor Y and into disc space or onto the spine. The procedure is known to those skilled in the art and known by differing names, such as the "XLIF" procedure (see "Extreme Lateral Interbody Fusion (XLIF): a novel surgical technique for anterior lumbar interbody fusion." By Ozgur, Aryan et al. in *Spine J.* 2006 July-August; 6(4):435-43, which is hereby incorporated by reference in its entirety.) Variations of the operation are also known as Direct Lateral Interbody Fusion (DLIF) and the like.

A second lateral corridor "Z" (FIG. 4) can be made from the flank, through the to posterior tissues lateral to the spine and onto the lateral aspect of the ipsilateral SAP of the superior and inferior vertebral bones to be immobilized. While Corridor Y and Corridor Z are shown schematically as exiting the skin 118 of the flank at two different sites, both corridors can be made through a single, common skin incision on the patient's flank. That is, a single incision is made through the skin 118 then a first sub-cutaneous trajectory is used to form the anterior Corridor Y and a second sub-cutaneous trajectory is used to form the posterior Corridor Z. The devices disclosed herein can be implanted into the posterior aspect of a functional spinal unit using a Corridor Z and, at the same operation; an implant can be placed into or onto the anterior column (including disc space) of the same functional spinal unit using a Corridor Y.

An exemplary method of device implantation is now illustrated. In an embodiment, a functional spinal unit FSU can be targeted for immobilization and fusion. FIG. 6A shows an illustrated spine with implant 305 positioned within the L4/L5 disc space. The level to be fused is the functional spinal unit FSU that includes the L4 and L5 vertebral bones and the intervening disc. An anterior column implant 305 is implanted into the L4/L5 disc space. In one particular embodiment, the anterior column implant is placed first, and the posterior column implant is subsequently placed. In one embodiment, the implant 305 is placed into the disc space using a true lateral, trans-psoas approach, wherein a lateral surgical corridor such as Corridor Y (FIG. 4) is used to access the disc space. A lateral corridor, such as Corridor Z, can be used to implant fixation device 105. In one embodiment, the anterior implant 305 is placed first. It is noted that a different level of the spine may be targeted for immobilization in another embodiment. For clarity of illustration, the vertebral bones of the illustrations presented herein are represented schematically and those skilled in the art will appreciate that actual vertebral bodies may include ana Comical details that are not shown in these figures. It is also understood that the totality of the operation—from selection of the target level to implant to the final placement of implant—can be performed under X-ray guidance. Further, the operation can be performed using percutaneous or minimally invasive surgical techniques with or without the aid of electrophysiological monitoring. The later include techniques such as electromyography (EMG), somato-sensory and motor evoked potential and the like. The techniques are intended to alert the operating surgeon to the presence of nerves and other neural elements within the surgical corridor. EMG identification of nerves permits the surgeon to navigate the surgical site with increased safety and to lessen the possibility of nerve injury.

A corridor Z is developed through the soft tissues from the skin incision to the lateral aspect of the SAP of the inferior vertebral bone of the FSU to be fused. The corridor can be developed using a variety of methods. As is known in the art, a wire or tissue dilator of small diameter may be percutaneously passed onto the lateral aspect of the target SAP using radiographic guidance. A dilator of larger diameter is then passed over the initial dilator. The process is repeated/reiterated with tissue dilators of progressively greater diameter until the desired size corridor is developed.

As an alternative step, an expandable retractor may be placed at a desired point of the iterative dilation process and the corridor can be expanded by direct expansion of the retractor. This process is illustrated in FIGS. 6-10. FIG. 6A shows the anterior column implant 305 having been placed into the L4/5 disc space. Implant 305 is placed the disc space by developing a lateral corridor Y (substantially similar to that of FIG. 4). Tissue dilators are placed from the skin, through the psoas muscle and guided onto the ipsilateral side of the L4/5 disc space. The soft tissue is sequentially dilated by passing dilators of progressively greater diameter and then positioning a tissue distractor as the final dilation step. (While sequential dilation is not shown for placement of implant 305 into anterior column, it is shown in FIGS. 6-10 for placement of implant 105 into the posterior column. The procedure for implant 305 placement is similar to that shown in FIGS. 6-10.) The distractor is opened and an L4/5 discectomy is performed. The implant 305 may be a fusion implant comprised of an internal cavity configured to house a bone graft material. The implant 305 is sized to extend fully from the ipsilateral lateral border of the implanted disc space (L4/5 in this illustration) to the contralateral lateral border of the disc space. In this way, the implant is positioned to rest upon the epipheseal ring of the vertebral bones that border the implanted disc space.

FIG. 6B shows a cylindrical tissue dilator 900 placed through a lateral corridor, such as Corridor Z, to a region that is substantially in between the ipsilateral SAP of L4 and ipsilateral SAP of L5. In one particular embodiment, the distal tip of the tissue dilator is positioned in proximity to the lateral aspect of the superior portion of the ipsilateral SAP of L5. FIGS. 7A-7B show the placement of a second tissue dilator 905 of greater diameter over the first tissue dilator 900. FIGS. 8A-8B show the placement of a third tissue dilator 910 of still greater diameter over the second tissue dilator 905. FIGS. 9A-9B illustrate the placement of a distraction device having tubular half-receptacles 915 that are of greater diameter than the third tissue dilator 910. Half-receptacles 915 can be advanced to target location by advancing the distractor atop the third tissue dilator 910. After placement of receptacles 915, the tissue dilators can be removed leaving a central channel 920 to the inter-spinous space (FIG. 9B). The distraction device 925 can be used to distract each half receptacle 915, as shown in FIG. 10A. FIG. 10B shows implant 105 immediately prior to advancement through channel 920 and onto the spine. (FIGS. 14-16 illustrate the implanted implant 105 after removal of the distraction device 925/receptacles 915.) Note that the distraction device 925 illustrated is generic and that one of ordinary skill in art can provide other distraction devices or even sequential tissue dilatation with progressively larger tissue dilators that may produce the expanded tissue channel for device implantation. Further, each dilatation step can be checked by intra-operative x-rays at the time of each tissue dilator placement. EMG (and other electrophysiological monitoring techniques) may be utilized to identify nerve elements and increase procedure safety.

An embodiment of the implant 105 is shown in perspective viewed in FIG. 11. The device is shown in orthogonal views in FIG. 12 and in sectional views in FIG. 13. Implant 105 includes a generally flat, elongate platform having a first surface 120 that contains bone-engaging members 1202 and an opposite, second surface 123. Members 1202 may generally have a tapered tip and members 1202 may be conical, pyramidal (with three or four sides, for example) or comprised of any appropriate geometric configuration.

The first surface 120 can have one or more elements 126. Elements 126 can contain an internal bore 1262 that extends in the direction of the long axis of element 126 and from its first end to its second end. While not shown, it is further contemplated that the circumferential wall of element 126 may contain at least one full thickness hole 1266 that extends from inner bore 1262 to the outer surface of element 126; the hole would permit the communication between the contents of bore 1262 and structures external to element 126. For example, bone forming material that is positioned within bore 1262 can form a bone fusion mass across the hole(s) and fuse with the bone members that are positioned outside of element 126 and in proximity to it. Finally, one or more full thickness bores 128 extend from surface 123 to 120.

In use, implant 105 is passed through the developed corridor Z (and through the distracted port of distractor 925) and onto the region between the lateral aspect of the ipsilateral SAP of the L4 and L5 vertebral bones. (Note, the term "ipsilateral" is used here to specify that the implant is positioned on the same side of the mid-sagittal plane (a vertical plane through the midline of the subject's body that divides it into a right half and a left half) as the site of the skin incision. Likewise, the term "contralateral" would specify a position on the opposite side of the mid-sagittal plane from the site of skin incision.) A view of the lateral surface of the spine is shown in FIG. 14 with implant 105 positioned in the posterior column and implant 305 positioned in the anterior column. FIG. 15 shows a view of the posterior aspect of the spine while FIG. 16 illustrates an oblique view. In one embodiment, a bone screw is positioned into bore 128 and used to fixate the adjacent L4/5 facet joint. That is, bone screw 201 is advanced from lateral to medial direction through the lateral wall of the ipsilateral SAP of the L5 vertebral bone, through the space of the ipsilateral L4/5 joint and into the ipsilateral IAP of the L4 vertebral bone. In this way, screw 201 rigidly affixes and immobilizes the ipsilateral L4/5 facet joint by providing screw fixation of the SAP of L5 onto the IAP of L4 of that joint. Note that spike members 1202 may be also driven into the lateral surface of the ipsilateral SAP of L5 in order to provide additional fixation of implant 105 onto bone.

Figure 18:
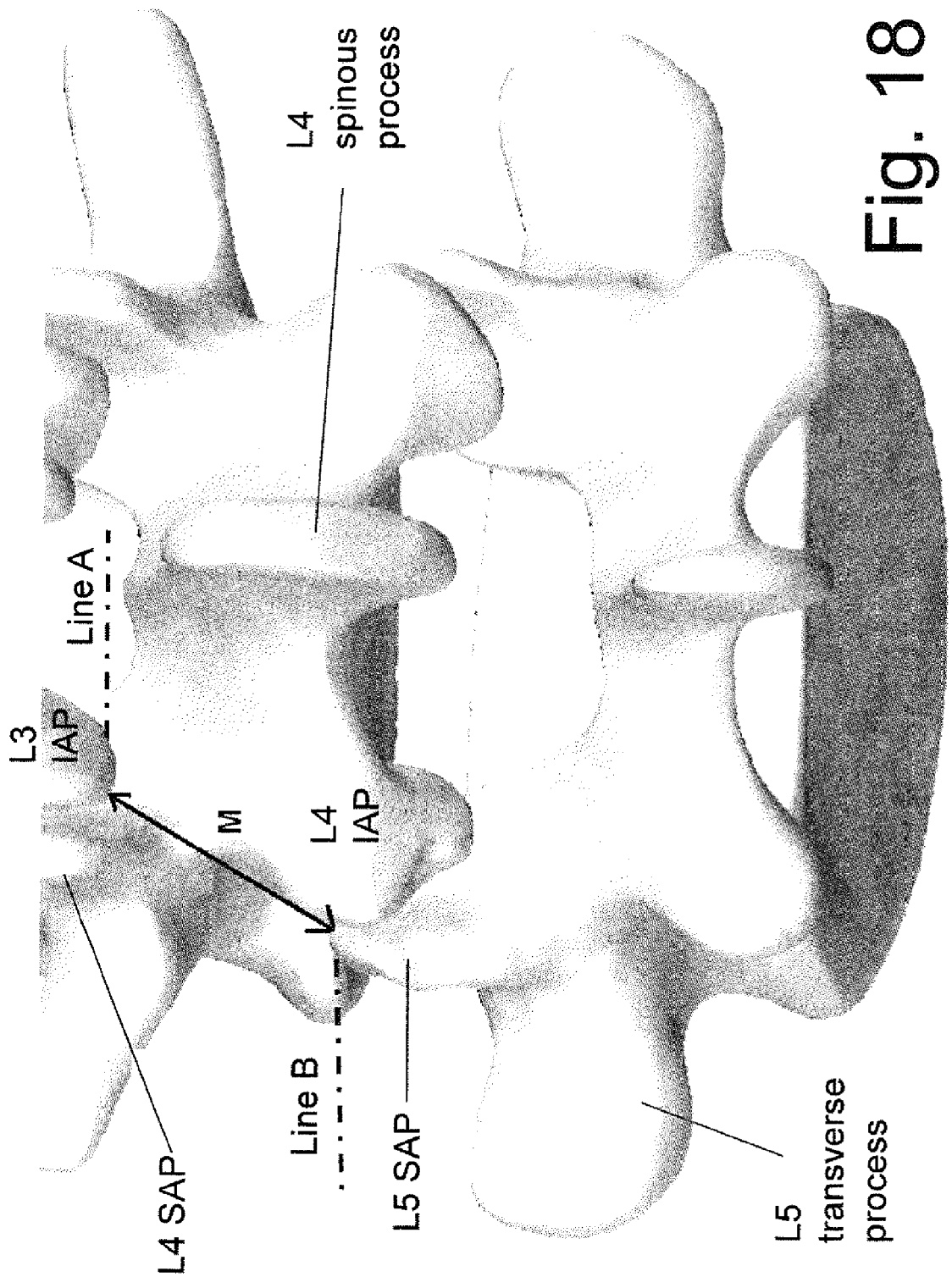
FIG. 18 is a posterior view of a subject spine illustrating an exemplary trajectory for advancement of the exemplary screw of FIG. 17A.

As can be seen in FIGS. 14 to 16, element 126 of the implant 105 is positioned posterior to the ipsilateral pars interarticularis of the L4 vertebral bone. In this position, the superior surface of element 126 abuts the inferior surface of the ipsilateral SAP of L4 vertebral bone whereas the inferior surface of element 126 abuts the superior surface of the ipsilateral SAP of the L5 vertebral bone. In this way, element 126 functions as a spacer that prevents the movement of the ipsilateral SAP of L4 towards the ipsilateral SAP of L5, and thus prevents vertebral extension. Element 126 also distracts the SAP of L4 and L5 from a lesser pre-implantation distance to a greater post-implantation distance—and the amount of distraction is dependent on the size of element 126 (i.e., the distance between the outer superior surface and outer inferior surface of element 206). Element 126 can have an internal bore, as shown, or it can be a solid member. Further, element 126 can be manufactured from a rigid material and/or a compressible/resilient material wherein the implant provides a cushioned stop to vertebral extension (whereas a rigid material would provide a "hard" stop to vertebral extension). In an embodiment, element 126 can have full thickness bore holes that extend from the exterior wall of element 126 to internal bore 1262. In this way, a bone forming material can be placed within bore 1262 and used to form a fusion across the full thickness bore holes of the exterior walls of element 126 so as to fuse the bone forming material of bore 1262 with the ipsilateral SAP of L4, the ipsilateral SAP of L5 or both. (Note that fusion with both the SAP of L4 and L5 would effectively fuse the L4 and L5 vertebral bones by forming a solid fusion mass from the inferior aspect of the SAP of L4 through bores 1262 and onto the SAP of L5.) In addition, a screw 205 may be also passed thorough bore 1262 (with or without concurrent bone forming material within bore 1262) and onto the spinous process of the L4 vertebral bone to provide an additional point of bony fixation for implant 105. Finally, note that the superior aspect of element 126 may be also positioned to abut the inferior aspect of the ipsilateral L3 IAP and so as to concurrently limit the extent of vertebral extension between the L3 and L4 vertebral bones. That is, element 126 extends across distance "M" (FIG. 18), which extends from the inferior surface of the ipsilateral L3 IAP (approximated by Line A) to the superior surface of the ipsilateral L5 IAP (approximated by Line B), and necessarily limits vertebral extension between the L3 and L5 vertebral bones.

It is further contemplated that a bone screw 211 may be used to fixate the contralateral L4/5 facet joint (i.e., the L4/5 facet joint that is contralateral to the site of skin incision). Screw 211 is shown in FIGS. 15 and 16. The screw is used to traverse the contralateral L4/5 facet joint from a medial to lateral direction, wherein the screw enters the contralateral L4 IAP, crosses the contralateral L4/5 facet joint space and then enters the contralateral L5 SAP. The trajectory of facet screw placement is shown in FIG. 17. To place screw 201 into the ipsilateral L4/5 facet, the lateral surface of the ipsilateral L5 SAP is identified on radiographic imaging. The screw 201 is advanced into the lateral surface of the ipsilateral L5 SAP at or about the region "X" of FIG. 17A (note that a lateral view of the spine is shown in FIG. 17A). The screw 201 is advanced medially through the facet joint space and into the ipsilateral L4 IAP. The placement trajectory of screw 201 is approximated by trajectory "A" of FIGS. 17B and 17C. (FIG. 17B illustrates the posterior aspect of the vertebral bones. FIG. 17C shows an axial plane view of the vertebrae.)

To place a screw 211 into the contralateral L4/5 joint, the lateral surface of the ipsilateral L5 SAP is identified on radiographic imaging and the screw 211 is passed immediately posterior to the ipsilateral L4/5 joint (which is concurrently posterior to the ipsilateral L5 SAP) as shown by region "Y" of FIG. 17A. The placement trajectory of screw 211 is approximated by trajectory "B" of FIGS. 17B and 18. Note that screw 211 is advanced through the L4/5 interspinous space (between the spinous processes of L4 and L5) and onto the medial aspect of the contralateral L4 IAP. The screw 211 is advanced into the contralateral L4 IAP, across the contralateral L4/5 facet joint space and into the contralateral L5 SAP. In an exemplary screw trajectory, screw 211 is aimed anteriorly after it passes the posterior edge of the ipsilateral L4/5 joint—as shown by trajectory "B" in FIG. 17C.

It is understood that while screws 201 and 211 have been shown implanted with implant 105, they may alternatively be implanted alone. That is, after placement of implant 305 through the lateral flank incision and corridor Y, the same lateral skin incision (or a separate but immediately adjacent lateral skin incision) is used to advance a facet screw 201 into the ipsilateral L4/5 facet joint as described above and shown in FIG. 17 (using trajectory A). Similarly, screw 211 is advanced (through the same skin incision used to place screw 201) across the vertebral midline and into the contralateral L4/5 facet joint using trajectory B and as described above and shown in FIG. 17. Note that these facet screws may be placed alone and without the concurrent placement of device 105. Whether or not device 105 is employed, a distractor may be positioned between the ipsilateral L4 SAP and ipsilateral L5 SAP to distract the posterior aspect of the L4 and L5 vertebral bones and decompress the spinal canal. The distraction is performed before placement of either screw 201 or 211. The distraction is then removed after placement of one or both screws 201 and 211, wherein the screws maintain the vertebral bones in the distracted position. Alternatively, another method of distraction of the posterior elements may be employed before facet screw placement. For example, the distraction device may be positioned within the inter-spinous space and used to distract the spinous process of the superior vertebral bone (i.e., L4) from the spinous process of the inferior vertebral bone (i.e., L5). After placement of facet screws 201 and/or 211, the distraction device may be removed (if intended for temporary use) or left positioned within the subjective (if intended for implantation).

Figure 19:
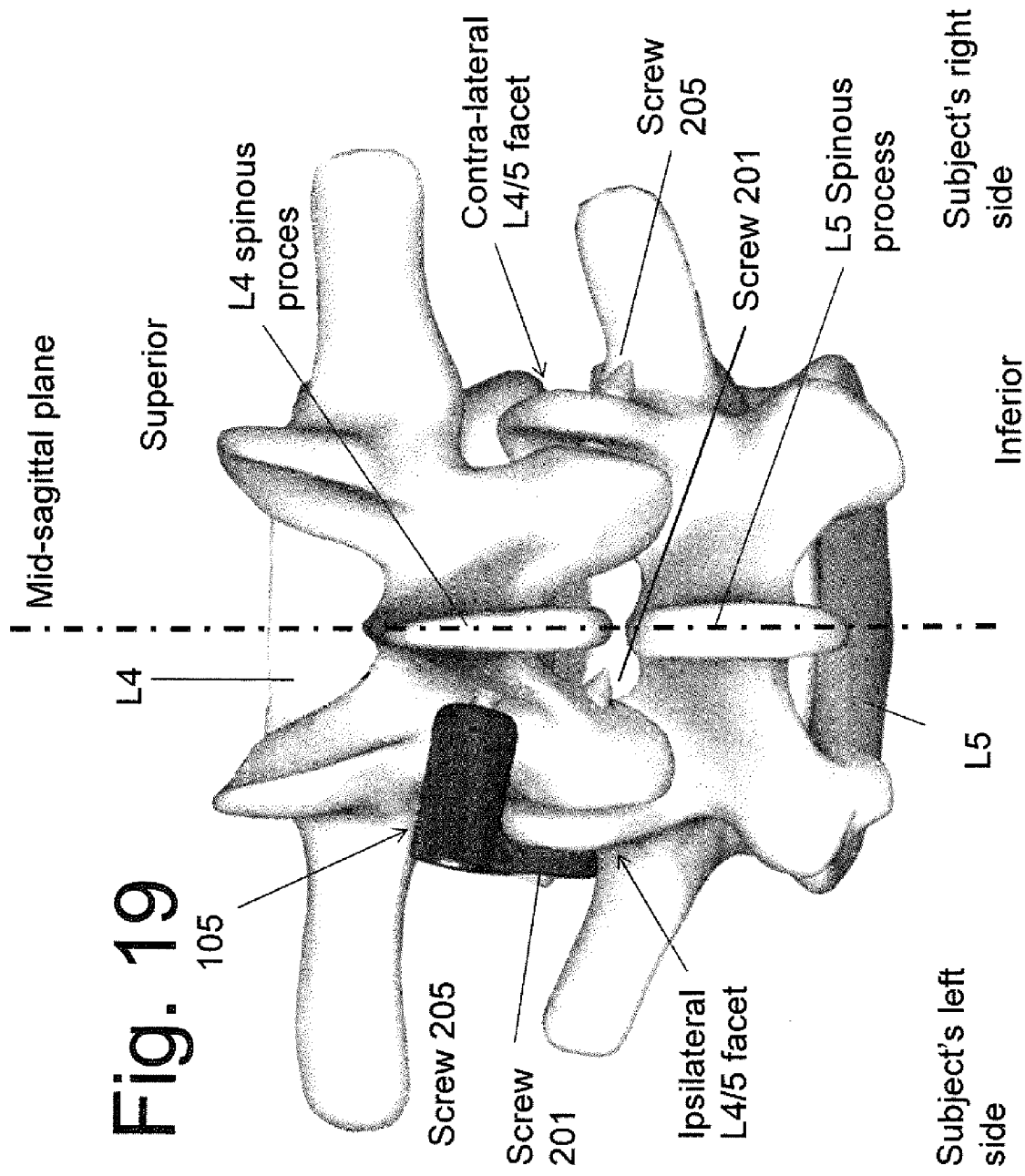
FIG. 19 is a posterior view of a subject spine illustrating an attachment of an exemplary implant.

FIG. 19 shows an embodiment of implant 105 wherein the contralateral L4/5 facet screw is placed directly through bore 1262. In this variation, a screw 205 may be passed thorough bore 1262 (with or without concurrent bone forming material within bore 1262) and into the contralateral L4/5 facet screw. In this trajectory, screw 205 may extend through a portion of the contralateral L4 lamina. Additional screws (such as independent screw 211) may be placed into the contralateral L4/5 facet joint, if desired. Additionally, element 126 can have full thickness bore holes that extend from the exterior wall of element 126 to internal bore 1262. In this way, a bone forming material can be placed within bore 1262 and used to form a fusion with the adjacent bone across the full thickness bore holes of the exterior walls of element 126.

In one embodiment, a locking feature/mechanism may be present to directly lock screw 201 and/or screw 205 to implant 105. The locking mechanism prevents screw back-out. The locking feature also rigidly immobilizes screw 201 and/or 205 to member 105 so that screw rotation is abolished. While illustrated here, a locking feature may be added to any device embodiment that is disclosed in this application. Further, any of the many known screw-to-plate locking mechanism may be alternatively used.

Figure 20:
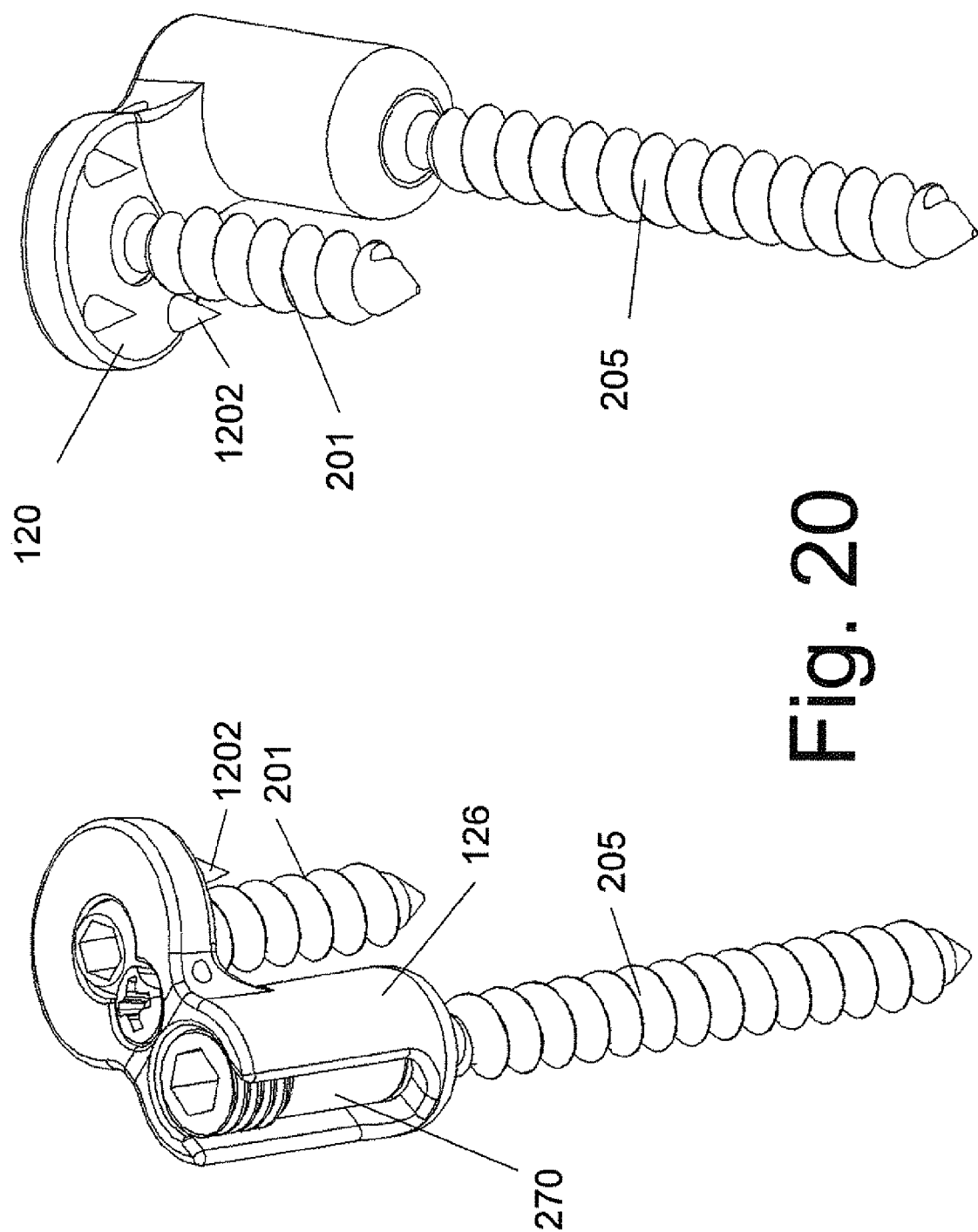
FIG. 20 is a perspective view of an exemplary assembled implant according to the present disclosure.
Figure 21:
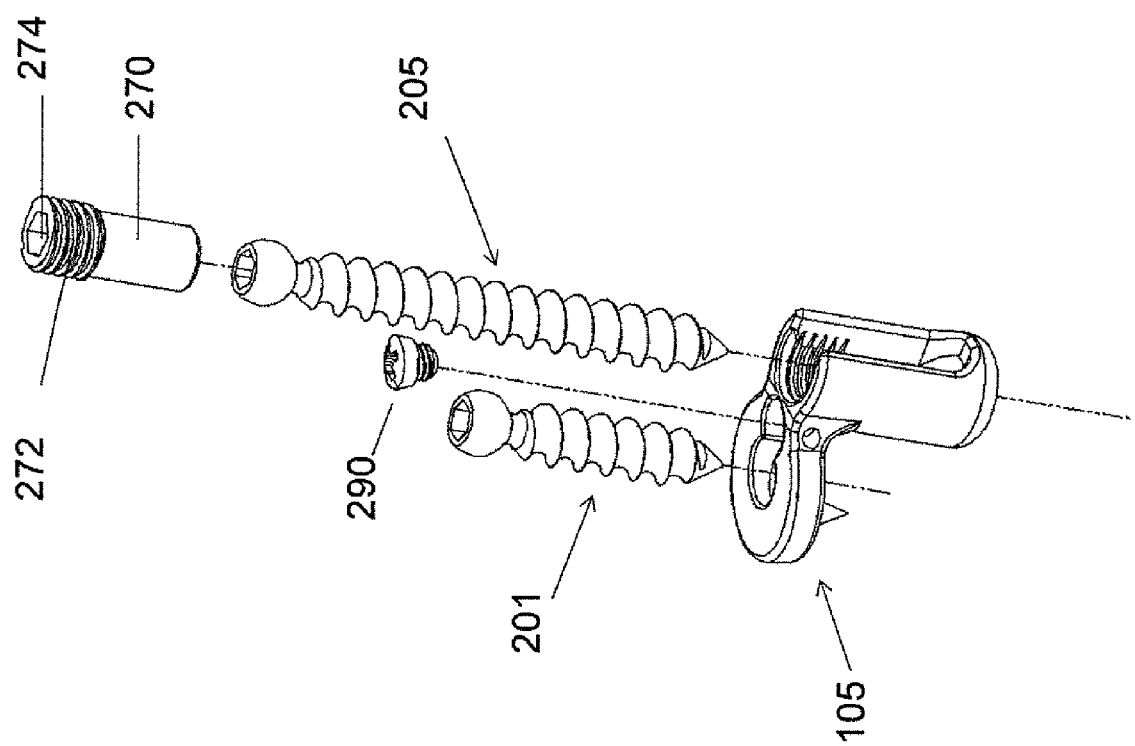
FIG. 21 is an exploded view of the exemplary implant of FIG. 20.
Figure 22B:
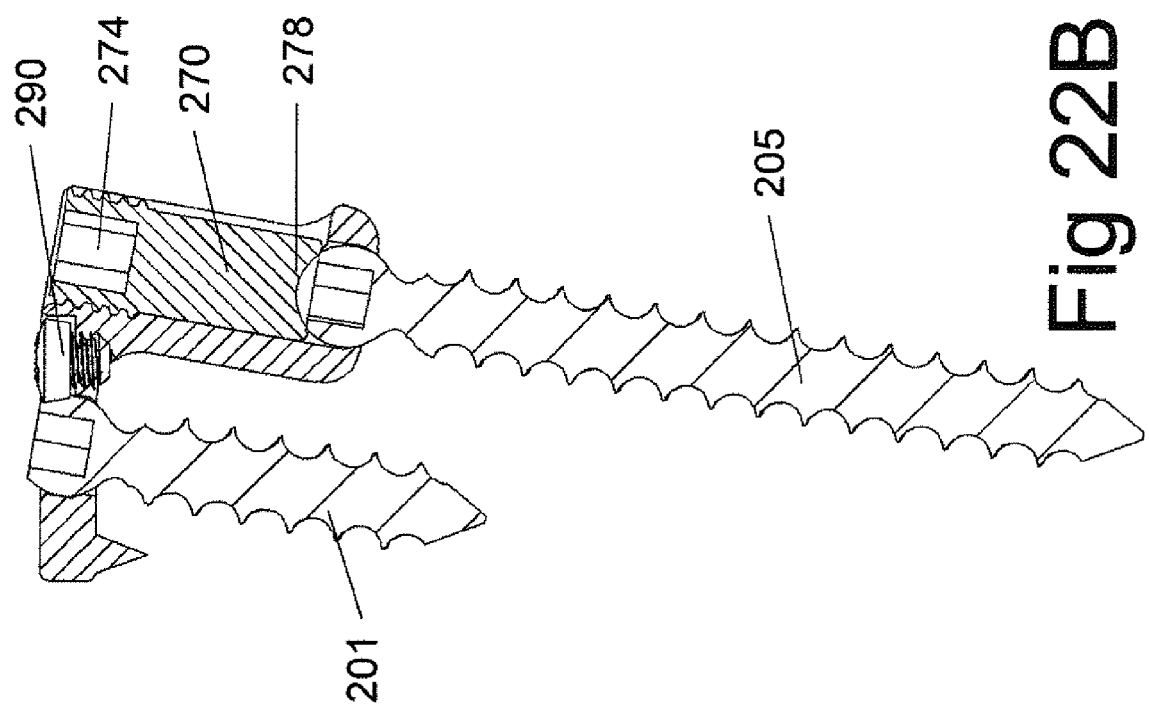
FIGS. 22A and 22B are sectional views of the exemplary implant of FIG. 20.
Figure 22A:
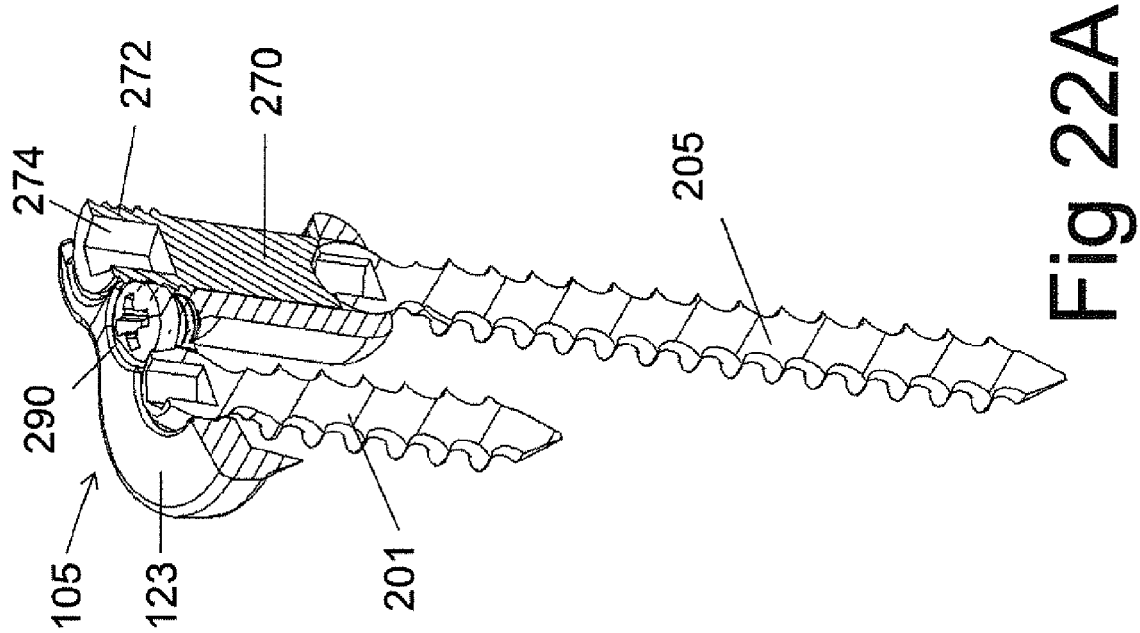

FIGS. 20-23 illustrate the embodiment of implant 105 that is shown affixed to bone in FIG. 19. The device contains locking features as will be discussed below. Implant 105 is shown in FIG. 20 (perspective views), FIG. 21 (exploded view) and FIG. 22 (sectional views). Implant 105 includes a generally flat, elongate platform having a first surface 120 that contains bone-engaging members 1202 and an opposite, second surface 123. Members 1202 may generally have a tapered tip and members 1202 may be conical, pyramidal or comprised of any appropriate geometric configuration.

As illustrated in FIG. 23, element 126 can contain an internal bore 1262 that extends in the direction of the long axis of the element 126 and from its first end to its second end. The circumferential wall of element 126 may contain one or more full thickness cut-outs (for example, 1266) that extend from inner bore 1262 to the outer surface of element 126. A first end of bore 1262 permits the passage of both the threaded shank and the head portions of screw 205, whereas the opposing second end of bore 1262 is sized to be of greater diameter than the shank of screw 205, but of lesser diameter than its head portion. In this way, the head of screw 205 is retained within bore 1262 when the screw 205 is passed there through. The wall of bore 1262 is at least partially threaded (1264). Locking member 270 is sized to fit within bore 1262 and has threads 272 that cooperatively engage threads 1264 of element 126. An indentation 274 is positioned at a first end of member 270 and configured to accept a driver that can exert a rotational force onto member 270. The opposing end of member 270 has a curvilinear or conical cavity 278 that permits the head portion of screw 205 to rotationally move therein. With forceful advancement of member 270 within bore 1262, the head portion of screw 205 can be captured and rigidly immobilized within cavity 278.

One or more full thickness bores 128 extend from surface 123 to 120 and are configured to accept the head portion of screw 201. The opening of bore 128 onto surface 120 is sized to be of greater diameter than the shank of screw 201, but of lesser diameter than its head portion. In this way, the head of screw 201 is retained within bore 128 when the screw 201 is passed there through. A locking screw 290 has threads 2902 and an indentation on its head portion that accepts a complimentary driver. A cut-out 2904 is positioned on a side of the head of screw 290—as shown in FIG. 24A. When cut-out 2904 is aligned with bore 280 (as shown in FIG. 24B), the head of screw 201 is free to rotate within bore 280. With rotation of screw 290 to the position illustrated in FIG. 24C, the head portion of screw 201 is at least retained within bore 280. The head of screw 201 may be rigidly immobilized relative to implant 105 when screw 290 is positioned as shown in FIG. 24C.

Figure 25:
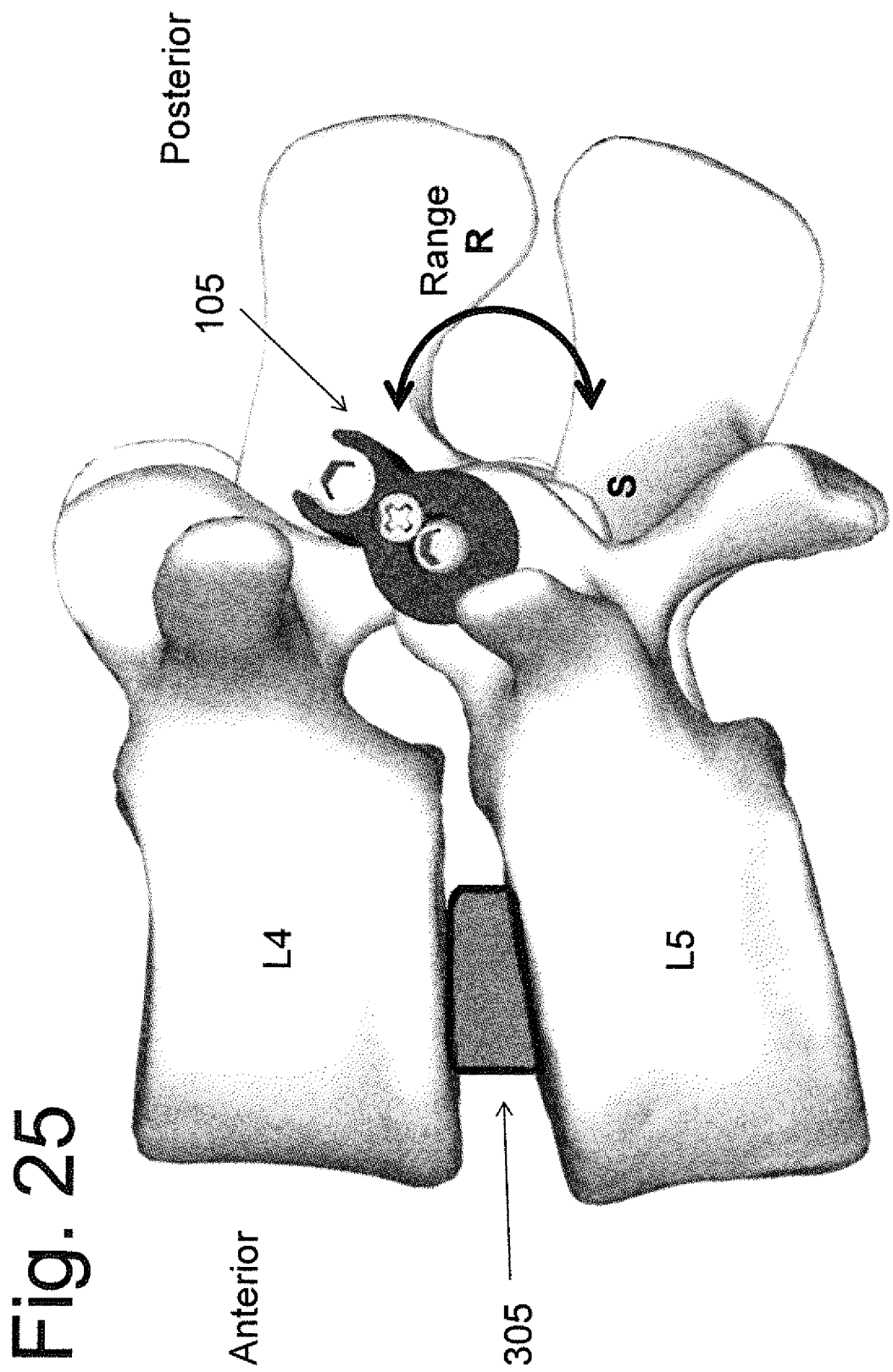
FIG. 25 is a lateral perspective view of a subject spine illustrating an attachment of an exemplary implant.

Implant 105 was shown attached to bone in FIG. 19 and again in FIG. 25. With surface 120 positioned to abut lateral surface of the ipsilateral L5 SAP, element 126 may be implanted at the illustrated position (posterior to the Pars interarticularis of L4), rotated to rest at position "S" (posterior to the Pars Interarticularis of L5), or positioned at any point there between (as depicted by range "R"). Since element 126 remains positioned substantially posterior the ipsilateral L4/5 facet joint, screw 205 is in position to directly reach and fixate the contralateral L4/5 facet joint.

In FIG. 26, element 126 is positioned substantially at the position "S" of FIG. 25 and separates the ipsilateral L5 SAP and ipsilateral S1 SAP. Screw 205 may positioned directly into the contra lateral L4/5 joint. Alternatively, screw 205 may be affixed to L5 spinous process. An additional screw 211 may be placed into the contra-lateral L4/5 facet joint. (Note that in this construct, L4/L5 FSU is immobilized and will be fused, while L5/S1 FSU remains mobile but with the vertebral extension thereof is limited by element 126.)

The disclosed device embodiments or any of their components can be made of any biologically adaptable or compatible materials. Materials considered acceptable for biological implantation are well known and include, but are not limited to, stainless steel, titanium, tantalum, combination metallic alloys, various plastics (such as PEEK and the like), resins, ceramics, biologically absorbable materials and the like. Any components may be also coated/made with osteo-conductive (such as demineralized bone matrix, hydroxyapatite, and the like) and/or osteo-inductive (such as Transforming Growth Factor "TGF-B," Platelet-Derived Growth Factor "PDGF," Bone-Morphogenic Protein "BMP," and the like) bio-active materials that promote bone formation. Further, any surface may be made with a porous ingrowth surface (such as titanium wire mesh, plasma-sprayed titanium, tantalum, porous CoCr, and the like), provided with a bioactive coating, made using tantalum, and/or helical rosette carbon nanotubes (or other carbon nanotube-based coating) in order to promote bone in-growth or establish a mineralized connection between the bone and the implant, and reduce the likelihood of implant loosening. Lastly, the system or any of its components can also be entirely or partially made of a shape memory material or other deformable material.

While this specification contains many specifics, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed. It is recognized that while certain embodiments of the disclosure are described in terms of a specific sequence of steps of a method, these descriptions are only illustrative of the broader methods, and may be modified as required by the particular application. Certain steps may be rendered unnecessary or optional under certain circumstances. Additionally, certain steps or functionality may be added to the disclosed embodiments, or the order of performance of two or more steps permuted. All such variations are considered to be encompassed within the disclosure and claimed herein.

While the above detailed description has shown, described, and pointed out novel features as applied to various embodiments, it will be understood that various omissions, substitutions, and changes in the form and details of the device or process illustrated may be made by those skilled in the art without departing from the contents of the disclosure. The foregoing description is of the best mode presently contemplated. This description is in no way meant to be limiting, but rather should be taken as illustrative of the general principles embodied herein. The scope of the present disclosure should be determined with reference to the claims.

What is claimed is:

1. A method for immobilization of a facet joint, comprising:
    approaching a lateral aspect of a first facet joint that comprises an articulation between an inferior articulating process of a superior vertebral bone and a superior articulating process of an immediately inferior vertebral bone;
    positioning a first segment of an orthopedic implant to abut a lateral side wall of said superior articulating process of said inferior vertebral bone;
    positioning a second segment of said orthopedic implant to extend medial to a lateral side wall of said first facet joint;
    coupling a first bone fastener to said first segment of said orthopedic implant;
    advancing said first bone fastener in a lateral to medial trajectory through the superior articulating process of said inferior vertebral bone and into the inferior articulating process of said superior vertebral bone;
    coupling a second bone fastener to said second segment of said orthopedic implant; and
    advancing said second bone fastener in a medial to a lateral trajectory and into a second facet joint positioned contralateral to said first facet joint.

2. The method of claim 1, further comprising actuating a locking feature to immobilize said first bone fastener to said first segment of said orthopedic implant.

3. The method of claim 1, further comprising actuating a locking feature to immobilize said second bone fastener to said second segment of said orthopedic implant.

4. The method of claim 1, wherein said second segment of said orthopedic implant is positioned between an ipsilateral superior articulating process of said superior vertebral bone and said superior articulating process of said inferior vertebral bone.

5. The method of claim 1, wherein said second bone fastener traverses an interspinous space.

6. The method of claim 1, further comprising using radiographic imaging.

7. The method of claim 1, further comprising forming a tissue corridor onto a lateral side of an intervertebral disc space that is positioned between said vertebral bones, said lateral side being ipsilateral to first facet joint.

8. The method of claim 7, further comprising advancement of a second orthopedic implant into said intervertebral disc space.

9. The method of claim 8, further comprising using electromyography during advancement of said second orthopedic implant.

10. The method of claim 1, wherein said act of approaching said first facet joint is at least partially accomplished by sequential advancement of dilators, each dilator having a greater diameter than a preceding one.

11. The method of claim 1, wherein said act of approaching said first facet joint is at least partially accomplished by advancement of a retractor device comprising a cylindrical segment that transitions from a lesser diameter to a greater diameter.

12. A method for immobilization of a superior vertebral bone relative to an immediately adjacent inferior vertebral bone and an intervertebral disc space contained therebetween, comprising:
    forming a first tissue corridor from a first skin incision onto an ipsilateral side of said intervertebral disc space,
    advancing an orthopedic implant through said first tissue corridor and into said intervertebral disc space;
    forming a second tissue corridor from a second skin incision and onto a lateral surface of a first facet joint that comprises an inferior articulating process of said superior vertebral bone and a superior articulating process of said inferior vertebral bone,
    advancing a first bone fastener in a lateral to medial trajectory sequentially through said superior articulating process of said inferior vertebral bone and then into said inferior articulating process of said superior vertebral bone, said articulating processes comprising said first facet joint;
    wherein each of said first facet joint and second tissue corridor are ipsilateral to said first skin incision.

13. The method of claim 12, further comprising passing a second bone fastener across a mid-sagittal plane that defines a vertebral midline and onto a medial aspect of a second facet joint.

14. The method of claim 13, wherein said second facet joint is positioned contralateral to said first facet joint and forms a second articulation between said superior and immediately inferior vertebral bones.

15. The method of claim 13, wherein said second bone fastener is advanced in a medial to lateral trajectory sequentially through an inferior articulating process of said superior vertebral bone and a superior articulating process of inferior vertebral bone.

16. The method of claim 12, further comprising using radiographic imaging.

17. The method of claim 12, further comprising using electromyography.

18. The method of claim 12, wherein said orthopedic implant is positioned to extend from said ipsilateral side of said intervertebral disc space and across a mid-sagittal line of said vertebral bones.

19. The method of claim 12, wherein said orthopedic implant is positioned into said intervertebral disc space prior to advancement of said first bone fastener into said first facet joint.

20. The method of claim 12, wherein said first skin incision is positioned in a flank segment of said subject.

21. The method of claim 12, wherein said second tissue corridor is at least partially developed by sequential advancement of dilators, each dilator having a greater diameter than a preceding one.

22. The method of claim 12, wherein said second tissue corridor is at least partially developed by said advancement of a retractor device comprising a cylindrical segment that transitions from a lesser diameter to a greater diameter.

23. A method to immobilize a superior vertebral bone relative to an immediately adjacent inferior vertebral bone, comprising:
    forming a first tissue corridor that extends from a lateral skin incision onto a first facet joint that comprises an inferior articulating process of said superior vertebral bone and a superior articulating process of said inferior vertebral bone, said first tissue corridor being ipsilateral to said first facet joint;
    passing a first fastener through said first tissue corridor and onto a lateral surface of said superior articulating process of said inferior vertebral bone; advancing said first fastener in a lateral to medial trajectory sequentially through said superior articulating process and into the inferior articulating process of said superior vertebral bone;
    driving said first fastener in a lateral to medial trajectory across each of said superior and inferior articulating processes of said first facet joint;
    advancing a second fastener through a tissue corridor ipsilateral to said first facet joint, across a mid-sagittal plane that defines a vertebral midline and onto a medial aspect of a second facet joint; and
    driving said second fastener in a medial to lateral trajectory across at least a segment of said second facet joint.

24. The method of claim 23, wherein said second facet joint is positioned contralateral to said first facet joint and forms an articulation between said superior and immediately inferior vertebral bones.

25. The method of claim 24, wherein said second bone fastener is advanced in a medial to lateral trajectory sequentially through an inferior articulating process of said superior vertebral bone and a superior articulating process of inferior vertebral bone of said second facet joint.

26. The method of claim 23, that further comprises positioning a first segment of a first orthopedic implant to abut said lateral surface of said superior articulating process of said inferior vertebral bone prior to advancement of said first fastener through said first tissue corridor.

27. The method of claim 26, that further comprises advancement of said first fastener at least partially through an aperture of said first orthopedic implant prior to driving said first fastener into said first facet joint.

28. The method of claim 23, that further comprises forming a separate tissue corridor onto a lateral side of an intervertebral disc space that is positioned between said vertebral bones.

29. The method of claim 28, wherein said lateral side of said intervertebral disc space is positioned ipsilateral to said first facet joint.

30. The method of claim 28, wherein said separate tissue corridor comprises a skin incision positioned in an ipsilateral flank.

31. The method of claim 28, further comprising advancement of a second orthopedic implant into said intervertebral disc space.

32. The method of claim 31, wherein said second implant is configured to permit fusion between said superior and immediately inferior vertebral bones.

33. The method of claim 31, further comprising using electromyography during advancement of said second orthopedic implant.

34. The method of claim 23, wherein said act of approaching said first facet joint is at least partially accomplished by sequential advancement of dilators, each dilator having a greater diameter than a preceding one.

35. The method of claim 23, wherein said act of approaching said first facet joint is at least partially accomplished by advancement of a retractor device comprising a cylindrical segment that transitions from a lesser diameter to a greater diameter.

36. The method of claim 23, further comprising using radiographic imaging.

* * * * *